US012263869B2

(12) United States Patent
Ganlath et al.

(10) Patent No.: US 12,263,869 B2
(45) Date of Patent: Apr. 1, 2025

(54) MEDICAL EMERGENCY DETECTION IN-VEHICLE CARETAKER

(71) Applicants: Toyota Jidosha Kabushiki Kaisha, Toyota (JP); Toyota Motor Engineering & Manufacturing North America, Inc., Plano, TX (US)

(72) Inventors: Akila C. Ganlath, Mountain View, CA (US); Rohit Gupta, Mountain View, CA (US); Paul Li, Mountain View, CA (US); Ziran Wang, Mountain View, CA (US); Kyungtae Han, Mountain View, CA (US); Nejib Ammar, Mountain View, CA (US); Satoshi Nagashima, Mountain View, CA (US)

( * ) Notice: Subject to any disclaimer, the term of this patent is extended or adjusted under 35 U.S.C. 154(b) by 344 days.

(21) Appl. No.: 17/725,297

(22) Filed: Apr. 20, 2022

(65) Prior Publication Data

US 2023/0339508 A1 Oct. 26, 2023

(51) Int. Cl.
*B60W 60/00* (2020.01)
*B60W 40/08* (2012.01)
*G16H 40/67* (2018.01)

(52) U.S. Cl.
CPC ........ *B60W 60/0016* (2020.02); *B60W 40/08* (2013.01); *B60W 60/005* (2020.02);
(Continued)

(58) Field of Classification Search
CPC ......... B60W 60/0016; B60W 2556/50; B60W 60/005; B60W 2540/221;
(Continued)

(56) References Cited

U.S. PATENT DOCUMENTS 8,085,139 B2    12/2011   Kanevsky et al.
9,149,236 B2 *  10/2015   Chun ................... A61B 5/0022
(Continued)

FOREIGN PATENT DOCUMENTS

CN    205302556 U    6/2016
CN    108113657 A    8/2019
(Continued)

OTHER PUBLICATIONS

"Connected Platform," retrieved from Internet at https://www.toyotaconnected.co.jp/en/service/connectedplatform.html, 6 pages.
(Continued)

*Primary Examiner* — Andrew Joseph Rudy
(74) *Attorney, Agent, or Firm* — Burbage Law, P.C.; Jon-Michael Burbage

(57) ABSTRACT

The disclosure includes embodiments for a medic system to respond to a medical condition of a vehicle occupant. A method according to some embodiments is executed by a processor. The method also includes determining, by the processor, that a driver of an ego vehicle is experiencing a debilitating medical condition. The method also includes overriding a protocol to decrease an autonomy level of the ego vehicle responsive to inattentiveness of the driver to a driving interface of the ego vehicle so that the driver can be inattentive to the driving interface and the autonomy level is not decreased. The method also includes modifying an operation of an autonomous driving system of the ego vehicle to increase the autonomy level of the ego vehicle to decrease a driving responsibility of the driver responsive to the debilitating medical condition.

20 Claims, 9 Drawing Sheets

(52) U.S. Cl.
CPC ..... *G16H 40/67* (2018.01); *B60W 2040/0818* (2013.01); *B60W 2540/221* (2020.02); *B60W 2540/229* (2020.02); *B60W 2556/50* (2020.02)

(58) Field of Classification Search
CPC ........... B60W 2540/229; B60W 40/08; B60W 2040/0808; G16H 40/67
USPC .......................................................... 701/23
See application file for complete search history.

(56) References Cited

U.S. PATENT DOCUMENTS

| | | | |
|---|---|---|---|
| 9,157,752 B1* | 10/2015 | Fernandez Garcia | B60R 25/30 |
| 10,395,332 B1 | 8/2019 | Konrardy et al. | |
| 10,535,341 B2 | 1/2020 | Penilla et al. | |
| 11,556,175 B2* | 1/2023 | Farooq | B60K 35/22 |
| 11,814,053 B2* | 11/2023 | Grentz | H04W 4/90 |
| 11,822,327 B2* | 11/2023 | Magzimof | B60W 60/007 |
| 11,897,513 B2* | 2/2024 | Kuranuki | B60W 60/0013 |
| 2004/0133082 A1 | 7/2004 | Abraham-Fuchs et al. | |
| 2014/0221781 A1 | 8/2014 | Schrauf et al. | |
| 2017/0364069 A1* | 12/2017 | Colella | G08G 1/096783 |
| 2019/0332902 A1 | 10/2019 | Gallagher et al. | |
| 2020/0216078 A1 | 7/2020 | Katz | |
| 2020/0401892 A1 | 12/2020 | Redding et al. | |
| 2021/0146957 A1* | 5/2021 | Kim | B60W 50/14 |
| 2021/0334645 A1 | 10/2021 | Pardeshi et al. | |
| 2023/0282114 A1* | 9/2023 | Kumar | G05D 1/0088 701/23 |
| 2023/0339492 A1* | 10/2023 | Hoh | B60W 50/14 |
| 2024/0184287 A1* | 6/2024 | Roberson | G05D 1/0077 |

FOREIGN PATENT DOCUMENTS

| | | |
|---|---|---|
| CN | 110426215 A | 11/2019 |
| CN | 109552289 B | 6/2020 |
| KR | 20180108033 A | 10/2018 |
| WO | 2020141485 A1 | 7/2020 |
| WO | 2021046172 A1 | 3/2021 |

OTHER PUBLICATIONS

"Teammate Advanced Drive Backgrounder," retrieved from Internet at https://pressroom.toyota.com/teammate-advanced-drive-backgrounder/, 6 pages, Jun. 3, 2021.

"Toyota's Discerning Approach to Car-making and Challenges for the Future," retrieved from Internet at https://www.youtube.com/watch?v=1SdRWBwDMrA, Video, Aug. 25, 2021.

* cited by examiner

MEDICAL EMERGENCY DETECTION IN-VEHICLE CARETAKER

BACKGROUND

The specification relates to providing a medic system to respond to a medical condition of an occupant of a vehicle. More specifically, some embodiments relate to providing a medic service to respond to sense, identify, and respond to a debilitating medical condition of a driver of a vehicle.

Modern vehicles broadcast vehicle-to-everything (V2X) messages that include digital data describing their locations, speeds, headings, past actions, and future actions, etc. Vehicles that broadcast V2X messages are referred to as "V2X transmitters." Vehicles that receive the V2X messages are referred to as "V2X receivers." The digital data that is included in the V2X messages can be used for various purposes including, for example, the proper operation of Advanced Driver Assistance Systems (ADAS systems) or autonomous driving systems which are included in the V2X receivers.

Modern vehicles include ADAS systems or automated driving systems. An automated driving system is a collection of ADAS systems which provides sufficient driver assistance that a vehicle is autonomous. ADAS systems and automated driving systems are referred to as "vehicle control systems." Other types of vehicle control systems are possible. A vehicle control system includes code and routines, and optionally hardware, which are operable to control the operation of some or all of the systems of a vehicle.

A particular vehicle that includes these vehicle applications is referred to herein as an "ego vehicle" and other vehicles in the vicinity of the ego vehicle are referred to as "remote vehicles."

Occupants of vehicles sometimes experience medical conditions when they are in a vehicle. For example, a driver of a vehicle having ADAS systems experiences a medical condition when they are driving the vehicle.

SUMMARY

Described herein are embodiments of a medic system, method, and a computer program product. See, for example, the medic system illustrated in FIGS. 1 and 2.

Occupants of vehicles sometimes experience medical conditions when they are in a vehicle. For example, a driver of a vehicle having ADAS systems experiences a medical condition when they are driving the vehicle. Sometimes the medical condition is debilitating. For example, the medical condition may impede or prevent a driver's ability to operate the vehicle.

In some embodiments, the driver may not be able to provide attention to the driving interface of the vehicle due to a medical condition. For example, the driver may not be able to place their hands on the steering wheel of the vehicle and hold their eyes at attention to the roadway viewable through the windows of the vehicle. A steering wheel is one example of a driving interface of a vehicle. Other examples include a touchscreen, a keyboard, a microphone, a processor-based computing device, and a stick steering system. In some embodiments, a driving interface is embedded with one or more of a torque sensor and a steering pressure sensor to detect a driver's attention (e.g., contact and responsiveness) to the driving interface. The cabin of the vehicle can include a cabin monitoring camera to monitor and trace a driver's gaze and eye orientation over time to generate images that are analyzable to determine whether the driver's attention is on the roadway. In this way, the onboard systems of the vehicle determine whether a driver is providing their attention to the driving interface of the vehicle.

A problem is that the current state of the art includes a protocol that disables or reduces the autonomous driving functionality of a vehicle whenever a driver is not providing attention to the driving interface of the vehicle sufficient to satisfy a threshold. For example, if a driver is not placing their hands on a driving interface of the vehicle (e.g., they are sleeping or reading their smartphone), then an onboard system of the vehicle provides an alert to the driver and reduces the autonomous driving functionality of the vehicle (e.g., one or more ADAS systems of the vehicle are disengaged or provide reduced ADAS functionality). This is an effective approach for discouraging a driver from not providing their attention to the driving interface of the vehicle. However, this approach is also problematic since the driver may not be providing their attention to the driving interface for a valid reason. For example, the driver may be experiencing a debilitating medical condition that prevents them from providing their attention to the driving interface of the vehicle. In these circumstances, reducing the autonomous driving functionality actually reduces safety since a driver that could benefit from increased driving assistance from the vehicle instead receives less driving assistance from the vehicle.

Described herein are embodiments of a medic system that solves the problem described above by causing a processor to execute one or more of the following steps: (1) detecting when a driver is experiencing a debilitating medical condition; (2) overriding the protocol that reduces the autonomy level of the vehicle, and (3) activating latent (or previously inactive) software and hardware included in the vehicle that increase or maximize the autonomy level of the vehicle based on the software and hardware that is onboard the vehicle. In this way, a vehicle including the medic system effectively maximizes the driving assistance provided to a driver of a vehicle when that driver is experiencing a debilitating medical condition cotemporaneous to their inattention to the driving interface of a vehicle. The medic system described herein beneficially provides such functionality in addition to other useful features which are also described herein and understandable to those having ordinary skill in the art of autonomous vehicles and intelligent transportation systems.

In some embodiments, the medic system includes code and routines that are stored on a non-transitory memory. In some embodiments, the code and routines of the medic system are configured, when executed by a processor (e.g., a processor of an onboard vehicle computer of an ego vehicle), to cause the processor to execute one or more of the steps depicted in methods 300, 400 of FIG. 3 and FIGS. 4A-4F, respectively.

Examples of the embodiments are now described. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method executed by a processor. The method also includes determining, by the processor, that a driver of an ego vehicle is experiencing a debilitating medical condition; overriding a protocol to decrease an autonomy level of the ego vehicle responsive to inattentiveness of the driver to a driving interface of the ego vehicle so that the driver can be inattentive to the driving interface and the autonomy level is not decreased, and modifying an operation of an autonomous driving system of the ego vehicle to increase the autonomy level of the ego vehicle to decrease a driving responsibility of the driver responsive to the debilitating medical condition. Other embodiments of this aspect include corresponding computer systems, apparatus, and computer programs recorded on one or more computer storage devices, each configured to perform the actions of the methods.

Implementations may include one or more of the following features. The method where inattentiveness includes a level of attention to the driving interface that fails to satisfy a threshold. Overriding the protocol enables the driver to be inattentive to the driving interface and the autonomy level of the ego vehicle is not decreased. Increasing the autonomy level of the ego vehicle includes maximizing the autonomy level of the ego vehicle. The method may include identifying a remote driver of the ego vehicle, disabling the driving interface of the ego vehicle, and enabling the remote driver to control a driving operation of the ego vehicle from a remote location. The method may include disabling the driving interface of the ego vehicle and causing the autonomous driving system of the ego vehicle to drive the ego vehicle to a safe location. The method may include causing the autonomous driving system of the ego vehicle to drive the ego vehicle to an original destination. The method may include initiating a telehealth appointment with a medical service provider. The method may include identifying a remote medical service provider and causing the ego vehicle to be driven to an intercept location to meet the remote medical service provider. The method may include identifying a remote driver of the ego vehicle, disabling the driving interface of the ego vehicle, and enabling the remote driver to control the operation of the ego vehicle from a remote location and drive the ego vehicle to the intercept location. The method may include disabling the driving interface of the ego vehicle and causing the autonomous driving system of the ego vehicle to drive the ego vehicle to the intercept location. The remote medical service provider is an ambulatory service provider. The intercept location is a geographic location on a roadway that is along an intercept course driven by the ego vehicle and the remote medical service provider. At least one step of the method is executed by a vehicular micro cloud. At least one step of the method is executed by a processor-based computing device selected from a group including: an edge server; a cloud server; and a roadside unit. A first degree of increase in the autonomy of the ego vehicle responsive to the debilitating medical condition is inversely proportional to a second degree of decrease in a driving ability of the driver based on the debilitating medical condition. The method may include determining how soon the debilitating medical condition will affect the driver. The method may include receiving feedback from the driver about one or more of whether they believe they are experiencing the debilitating medical condition and an immanency of the debilitating medical condition to affect their driving ability. Implementations of the described techniques may include hardware, a method or process, or computer software on a computer-accessible medium.

One general aspect includes a system including a non-transitory memory and a processor communicatively coupled to the non-transitory memory, where the non-transitory memory stores computer readable code that is operable, when executed by the processor, to cause the processor to execute steps including: determining that a driver of an ego vehicle is experiencing a debilitating medical condition; overriding a protocol to decrease an autonomy level of the ego vehicle responsive to inattentiveness of the driver to a driving interface of the ego vehicle so that the driver can be inattentive to the driving interface and the autonomy level is not decreased; and modifying an operation of an autonomous driving system of the ego vehicle to increase the autonomy level of the ego vehicle to decrease a driving responsibility of the driver responsive to the debilitating medical condition. Other embodiments of this aspect include corresponding computer systems, apparatus, and computer programs recorded on one or more computer storage devices, each configured to perform the actions of the methods.

One general aspect includes a computer program product including computer code stored on a non-transitory memory that is operable, when executed by a processor, to cause the processor to execute operations including determining that a driver of an ego vehicle is experiencing a debilitating medical condition; overriding a protocol to decrease an autonomy level of the ego vehicle responsive to inattentiveness of the driver to a driving interface of the ego vehicle so that the driver can be inattentive to the driving interface and the autonomy level is not decreased, and modifying an operation of an autonomous driving system of the ego vehicle to increase the autonomy level of the ego vehicle to decrease a driving responsibility of the driver responsive to the debilitating medical condition. Other embodiments of this aspect include corresponding computer systems, apparatus, and computer programs recorded on one or more computer storage devices, each configured to perform the actions of the methods.

Connected vehicles include vehicles that have a communication unit that is operable to send and receive wireless messages via a network such as the network 105 depicted in FIG. 1. Connected vehicles are referred to herein as "vehicles" or "connected vehicles."

An optional feature of the medic system is a vehicular micro cloud. Vehicles form vehicular micro clouds to assist them in completing vehicular cloud services that they would not otherwise be able to complete individually due, for example, to the limitations of their onboard computer hardware, software, bandwidth, and/or network access. A vehicle that is a member of a vehicular micro cloud is referred to as a "member." A vehicular micro cloud includes a plurality of members. A vehicular cloud service is provided by the members of the vehicular micro cloud completing vehicular micro cloud tasks (herein, "tasks" or "vehicular micro cloud tasks") that are assigned to them by a "hub vehicle" that is a member of the vehicular micro cloud and also the leader of the vehicular micro cloud. The completion of the vehicular cloud service benefits one or more of the members of the vehicular micro cloud. Providing vehicular cloud services is a primary purpose that vehicles form and maintain vehicular micro clouds.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

Figure 1:
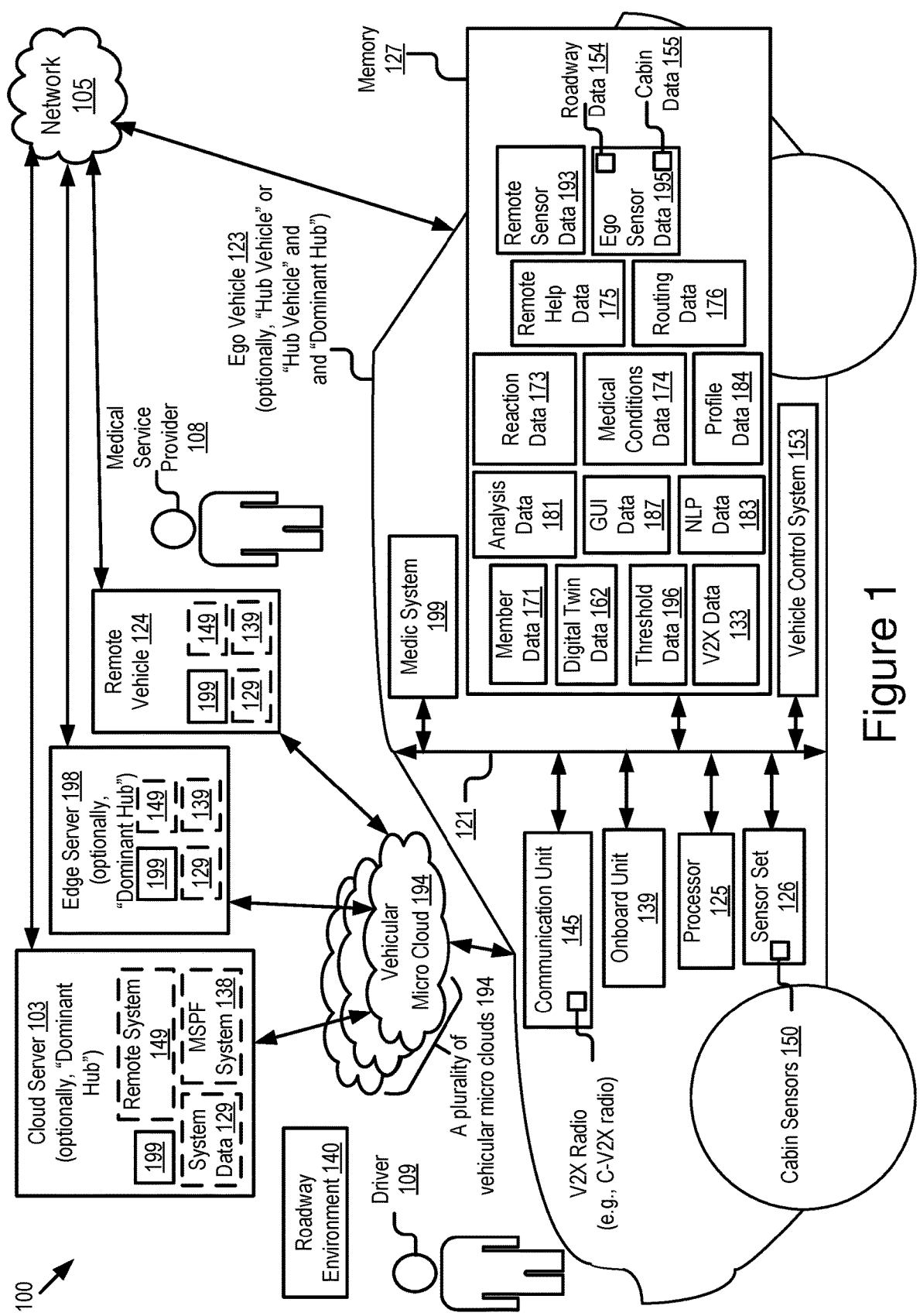
FIG. 1 is a block diagram illustrating an operating environment for a medic system according to some embodiments.

Described herein are embodiments of a medic system. The functionality of the medic system is now introduced according to some embodiments.

Vehicles include onboard sensors that constantly record sensor data describing sensor measurements of the onboard sensors. These sensor measurements describe conditions inside the cabin of the vehicle as well as sensor measurements of the external environment of the vehicle. In some embodiments, the sensor data is time stamped so that individual sensor measurements recorded by the onboard sensors include a time stamp describing the time when the sensor measurement was recorded. Time data includes digital data that describes the time stamps for the sensor measurements that are described by the sensor data. Vehicles transmit V2X messages to one another.

The sensor data includes digital data describing the sensor measurements recorded by the onboard sensors (e.g., the sensor set). In some embodiments, instances of sensor data describe one or more sensor measurements, and the instances of sensor data are timestamped with time data to indicate the time when the one or more sensor measurements were recorded.

Sensors that record measurements inside the cabin of the vehicle are referred to as cabin sensors. An example of cabin sensors according to some embodiments includes the cabin sensors 150 depicted in FIGS. 1 and 2. The cabin sensors include one or more sensors. An example of the cabin sensors according to some embodiments includes one or more of the following: a microphone; a steering pressure sensor; a steering wheel torque sensor; a steering wheel pulse oximeter (e.g., one or more pulse oximeters embedded within a steering wheel); a steering wheel blood pressure monitor (e.g., one or more blood pressure monitors embedded within a steering wheel); a seat temperature sensor (e.g., a temperature sensor embedded within a seat of a vehicle); a seat weight sensor; a seat pressure sensor; and one or more cabin monitoring cameras (and a non-transitory memory storing a set of object priors used by the medic system to recognize patterns within the images captured by the cameras, an artificial intelligence algorithm trained to recognize patterns within the images, or some other image or pattern recognition technique). In some embodiments, the cabin sensors are included in a sensor set of a vehicle. An example of a sensor set according to some embodiments includes the sensor set 126 depicted in FIGS. 1 and 2.

A steering pressure sensor includes an electronic sensor that records the pressure applied to the steering wheel by a driver of the ego vehicle. The measurement recorded by the steering pressure sensor indicates, for example, whether a driver has their hands on the steering wheel (e.g., whether they are providing their attention to a driving interface of the ego vehicle). In some embodiments, the measurement recorded by the steering pressure sensor is a factor in determining whether the driver is experiencing a medical condition or whether their medical condition is debilitating.

A steering wheel torque sensor includes an electronic sensor that records the torque applied to the steering wheel of the ego vehicle. The measurement recorded by the steering wheel torque sensor describes, for example, an amount of torque that a driver is applying to the steering wheel. This torque measurement is an indication of the driver's responsiveness to an event. In some embodiments, the measurement recorded by a steering wheel torque sensor indicates an attention of a driver to the driving interface of the ego vehicle. In some embodiments, the measurement recorded by the steering wheel torque sensor is a factor in determining whether the driver is experiencing a medical condition or whether their medical condition is debilitating.

A steering wheel pulse oximeter includes one or more pulse oximeters embedded within a steering wheel. The measurement recorded by the steering wheel pulse oximeter describes an amount of oxygen (e.g., oxygen saturation) within the blood of a driver of the ego vehicle. In some embodiments, the measurement recorded by the steering wheel torque sensor is a factor in determining whether the driver is experiencing a medical condition or whether their medical condition is debilitating. For example, the oxygen content of blood is a factor in many different medical diagnoses. In some embodiments, the blood oxygen content measurement is used by the medic system to calculate other measurements that are relevant to diagnosing the driver with a medical condition.

A steering wheel blood pressure monitor includes one or more blood pressure monitors embedded within a steering wheel. The measurement recorded by the steering wheel blood pressure monitor describes a blood pressure of a driver of the ego vehicle. In some embodiments, the measurement recorded by the steering wheel blood pressure monitor is a factor in determining whether the driver is experiencing a medical condition or whether their medical condition is debilitating. For example, blood pressure is a factor in many different medical diagnoses. In some embodiments, the blood pressure measurement is used by the medic system to calculate other measurements that are relevant to diagnosing the driver with a medical condition.

A seat temperature sensor includes a temperature sensor embedded within a seat of the ego vehicle. The measurement recorded by the seat temperature sensor describes a temperature of a driver or other occupant of the ego vehicle. In some embodiments, the measurement recorded by the seat temperature sensor is a factor in determining whether the driver is experiencing a medical condition or whether their medical condition is debilitating. For example, body temperature is a factor in many different medical diagnoses. In some embodiments, the body temperature measurement is used by the medic system to calculate other measurements that are relevant to diagnosing the driver with a medical condition.

A seat weight sensor is an electronic weight sensor embedded within a seat of the ego vehicle. The measurement recorded by the seat weight sensor describes a body weight of a driver or other occupant of the ego vehicle. In some embodiments, the measurement recorded by the seat weight sensor is a factor in determining whether the driver is experiencing a medical condition or whether their medical condition is debilitating. For example, body weight is a factor in many different medical diagnoses. In some embodiments, the body weight is used by the medic system to calculate other measurements such as body mass index.

A seat pressure sensor is an electronic pressure sensor embedded within a set of the ego vehicle. The measurement recorded by the seat pressure sensor describes a pressure applied to a seat of the ego vehicle. In some embodiments, the measurement recorded by the seat pressure sensor is a factor in determining one or more of the following: whether the driver is providing attention to the driving interface of the ego vehicle; whether the driver or other occupant is experiencing a medical condition; and whether such a medical condition is debilitating. For example, if a driver is not seated in their seat, or if the seat pressure experiences a series of rapid changes, this may be a sign that they are experiencing a seizure, heart attack, convulsion, etc. Different known patterns described by the medical conditions data 174 may correspond to different medical conditions. In some embodiments, the seat pressure sensor is used to measure blood pressure or some other medically relevant calculation. In another example, in some embodiments if no pressure is sensed in by the seat pressure sensor, then this is one factor among others that indicates that the driver is not seated and therefore not providing attention to the driving interface of the ego vehicle. Other examples are possible.

A cabin monitoring camera includes a digital camera that monitors the occupants of the vehicle. For example, the cabin monitoring camera captures images and/or videos. The images and/or videos are described by the ego sensor data. A non-transitory memory accessible by a processor of the ego vehicle stores object priors, a trained artificial intelligence (AI) network (e.g., a neural network or some other AI network), or some other references (i.e., reference data, which in some embodiments is an element of the medical conditions data 174) that is configured for use by the medic system 199 to identify patterns within the images and/or videos.

For example, the medic system 199 includes an AI algorithm that includes a neural network that is trained to identify medical conditions based on images inputted to the neural network. The medic system 199 receives a set of ego sensor data as an input including a set of images and the medic system 199 inputs these images to the neural network which then identifies one or more medical conditions being experienced by particular occupants of the ego vehicle (e.g., the driver of the ego vehicle) based the medic system 199 determining that the images depict a pattern that is known to correspond to the one or more medical conditions, which may or may not also be classified as one or more debilitating medical conditions.

In some embodiments, the medical conditions data 174 includes a database of medical conditions and one or more of the sensor measurements, medical symptoms, and medical history (e.g., profile data information) that correspond to diagnosing the presence of these medical conditions.

In some embodiments the medic system compares the images and/or videos to a set of object priors to identify medical conditions and/or debilitating medical conditions depicted in the images and/or videos.

In some embodiments, the processing of the image and/or videos is done by a server (e.g., the cloud server or the edge server) or a network-enabled processor-based computer device that is present on a roadside device such as a roadside unit. For example, the roadside unit includes an edge server that includes an instance of the medic system that processes ego data to identify patterns consistent with one or more medical conditions that may also be debilitating.

A microphone includes a conventional microphone. The driver or other occupant of the vehicle can use the microphone to provide direct information to the medic system. For example, the medic system causes a speaker or graphical display of the ego vehicle to query the driver for information (e.g., "Are you feeling sick?," "Can you still drive?," "Are you feeling a sharp pain in your right arm?," "Do you want to talk to a doctor in a telehealth visit with a doctor?" and any other query that provides information relevant to determining a medical condition of the driver and the preference of the driver for responding to their condition) and the medic system uses this input (which is itself described by the ego sensor data) as a factor in determining whether the driver is experiencing a medical condition and/or whether the medical condition is debilitating. In some embodiments, the medic system includes a natural language processing (NLP) system that is operable to receive ego data describing the occupant's inputs to the microphone (e.g., recordings of their spoken language) and process these inputs to determine what the driver has said responsive to queries and convert this information into an input that is usable by the medic system to provide its functionality. The NLP data 183 depicted in FIG. 1 includes digital data that is necessary for the NLP system to provide its functionality. For example, the NLP data 183 includes digital data that describes information that is used by the NLP system to receive inputs from a microphone and convert this data to digital data describing what is said in the audio recorded by the microphone (e.g., natural language).

The NLP data 183 also includes digital data that is sued by the NLP system and/or the medic system 199 to determine what of this natural language is relevant to a determination of one or more of a medical condition, how the occupant prefers to respond to the medical condition, and any other relevant information such as a medical history of the occupant, insurance information for the occupant, billing information, next of kin, etc.

In some embodiments, one or more of a microphone, a graphical user interface, an electronic display device are used by the occupant to participate in a telehealth appointment with a medical service provider to respond to the medical condition or symptoms of the driver. For example, the medic system determines that an appropriate respond to a medical condition (or an inconclusive result in determining the medical condition) is to initiate a telehealth visit.

Examples of an electronic display device include one or more of the following: a touch screen; an electronic display; a heads-up display; and any other electronic display device. In some embodiments, the electronic display device is embedded in a surface of the ego vehicle such as a rear-view mirror, a side mirror, a windshield, etc.

GUI data includes digital data that describes information that controls what is displayed on a graphical user interface of the ego vehicle (e.g., a graphical display of an infotainment system or a heads-up display unit). An example of the GUI data according to some embodiments includes the GUI data 187 depicted in FIG. 1.

In some embodiments, a non-transitory memory of the ego vehicles stores profile data for one or more occupants or drivers of the ego vehicle. Profile data includes digital data that describes a profile for an occupant. The profile includes a medical history of the occupant and any other information that is useful for providing them help with diagnosing a medical condition or helping them receive help responsive to a detected medical condition or a set of symptoms. For example, the profile data describes one or more of the following: medical history of the occupant; insurance information for the occupant; billing information for the occupant; next of kin for the occupant; past symptoms detected by the medic system for the occupant and the dates of these detections; and any other information that is useful for providing the occupant help with diagnosing a medical condition or helping them receive help responsive to a detected medical condition or a set of symptoms. An example of the profile data according to some embodiments includes the profile data 184 depicted in FIG. 1.

Analysis data includes digital data that describes the output or process of any analysis executed by the medic system 199. For example, the analysis data describes any output executed following the execution of any method described herein (e.g., methods 300, 400).

The following are examples of analysis data according to some embodiments. In some embodiments, the analysis data describes the results of an image recognition process, or an NLP process executed by the medic system (or the results of any step included in these processes). In some embodiments, the analysis data describes the results of any process or step included in a digital twin analysis executed by the medic system. In some embodiments, the analysis data describes the results of any process or step included in a routing process executed by the medic system or a GPS system of the ego vehicle. In some embodiments, the analysis data describes the results of any process or step included in providing ADAS functionality or autonomous driving functionality executed by the medic system or vehicle control system of the ego vehicle. In some embodiments, the analysis data describes the results of any process or step included in providing mobility services platform functionality (MSPF) executed by the medic system and/or the MSPF system 138 depicted in FIG. 1. These examples are illustrative; other examples are possible.

In some embodiments, analysis data includes digital data that describes the output of any determination or analysis described herein. An example of the analysis data according to some embodiments includes the analysis data 181 depicted in FIG. 1.

In some embodiments, the analysis data describes a set of symptoms (e.g., symptoms of a medical condition or elements of a medical diagnosis) present in the ego sensor data 195 as detected by the cabin sensors 150 of the ego vehicle 123. Medical conditions data includes digital data used to identify patterns within the set of symptoms that correspond to a medical condition. The medical conditions data also describes which of these medical conditions are, or are not, debilitating. An example of the medical conditions data according to some embodiments includes the medical conditions data 174 depicted in FIG. 1.

In some embodiments, the medical conditions data includes a trained AI network (e.g., a trained neural network) that is operable to identify patterns within the set of symptoms and, in this way identify both medical conditions and, among these medical conditions, those which are debilitating.

Reaction data includes a set of remedial action plans to respond to different medical conditions. In some embodiments, these remedial action plans are designed or approved by a set of medical service providers such as one or more medical doctors. In some embodiments, these remedial action plans are designed responsive at least in part to a set of digital twin simulations and configured to provide the occupant with the best possible medical outcome based on both their medical condition(s) and the roadway environment that they are present within (e.g., congested roads with a long travel time to a hospital, etc.). In some embodiments, the remedial action plans are determined by the medic system and approved in real time or near real time by a medical service provider. In some embodiments, the medic system or an edge server, cloud server or some other entity determines some or all of the reaction plans. An example of the reaction data according to some embodiments includes the reaction data 173.

Routing data includes digital data that corresponds to a route for the ego vehicle to drive responsive to a remedial action plan determined by the medic system. The route includes, for example, one or more of the following depending on the medical condition of the occupant: smoothly driving to the side of the road; driving to a medical service provider (e.g., a hospital or clinic); driving on an intercept course with a roadside medical service provider (e.g., an ambulance or some other ambulatory service provider); driving on an original route of the ego vehicle (e.g., while the occupant takes other action such as scheduling a doctor's appointment, participating in a telehealth visit, etc.); and any other driving route specified or consistent with the reaction data corresponding to the medical condition of the occupant.

Remote help data includes digital data provided by one or more of a remote medic system located on another entity (e.g., the cloud server, the edge server, etc.) or an MSPF system operated by the other entity. For example, the medic system of the ego vehicle is unable to diagnose the occupant with a medical condition with sufficient certainty to satisfy a threshold and so the medic system offloads responsibility to another entity with a computational advantage relative to the medic system of the ego vehicle. The other entity provides remote help data describing information that specifies the medical condition or provides other help to the medic system of the ego vehicle. In some embodiments, the remote help data includes reaction data, digital twin data, analysis data, or some other digital data that helps the medic system of the ego vehicle to provide its functionality.

An example of the remote help data according to some embodiments includes the remote help data 175 depicted in FIG. 1.

The MSPF system 138 includes code and routines that are operable to provide mobility services platform functionality to the ego vehicle and other endpoints of a network such as the network 105. In some embodiments, the MSPF system 138 enables the ego vehicle or the medic system 199 to receive any computational benefit described herein as being provided by a third party or remote endpoint. In some embodiments, and endpoint of the network 105 includes an MSPF system 138. In some embodiments, one or more endpoints of the network 105 include an instance of the MSPF system 138.

In some embodiments, the remote help data includes any digital data or code and routines that are necessary to allow the ego vehicle to be operated by a remote third party such as a remote system. The remote system includes a human or software that is operable to operate the ego vehicle as a drone from a remote location. In some embodiments, the remote operation of the ego vehicle is facilitated through the MSPF system. An example of the remote system according to some embodiments includes the remote system 149 depicted in FIG. 1. In some embodiments, the remedial action plan for a medical condition given the current roadway conditions dictates that the remote system should operate the ego vehicle for a period of time (e.g., until the ego vehicle arrives at a specified location such as a medical service provider).

Ego sensor data includes digital data that describes the sensor measurements recorded by the sensor set of an ego vehicle. An example of the ego sensor data in some embodiments includes the ego sensor data 195 depicted in FIG. 1. In some embodiments, the sensor measurements described by the ego sensor data 195 are time stamped. Time data includes digital data that describes the time stamps for the sensor measurements described by the ego sensor data 195.

The ego sensor data includes two categories of sensor data: roadway data; and cabin data. These are now described.

Roadway data includes digital data that describes the sensor measurements recorded by the sensor set of an ego vehicle and describing the conditions external to the ego vehicle. For example, the roadway data describes the roadway environment that includes the ego vehicle. An example of the roadway data according to some embodiments includes the roadway data 154 depicted in FIG. 1.

Cabin data includes digital data that describes the sensor measurements recorded by the cabin sensors of an ego vehicle and describing the conditions inside the cabin of the ego vehicle. For example, the cabin data describes information relevant to determining the medical condition of an occupant of the ego vehicle. An example of the cabin data according to some embodiments includes the cabin data 155 depicted in FIG. 1.

Remote vehicles also include sensor sets similar to those included in the ego vehicle. Remote sensor data includes digital data that describes the sensor measurements recorded by the sensor set of a remote vehicle. An example of the remote sensor data in some embodiments includes the remote sensor data 193 depicted in FIG. 1. In some embodiments, the sensor measurements described by the remote sensor data 193 are time stamped. Time data includes digital data that describes the time stamps for the sensor measurements described by the remote sensor data 193.

In some embodiments, the remote sensor data 193 is beneficial, for example, because it helps the medic system have a better understanding of roadway environment of the ego vehicle (e.g., because the sensors of the remote vehicle are more accurate than those of the ego vehicle or have a different perspective relative to the sensors of the ego vehicle due to their different orientation or proximity relative to the sensors of the ego vehicle). In some embodiments, the remote sensor data 193 is used by the medic system 199 to enhance or confirm the accuracy of the roadway data 154 and then determine responses to the detected medical condition of the occupant (e.g., pulling over to the side of the road, driving to the hospital, driving on an intersect course to an ambulatory service provider or some other roadside medical service provider).

In some embodiments, the remote sensor data 193 is transmitted to the ego vehicle via V2X messages. V2X messages include V2X data in their payload. The V2X data includes, among other things, the sensor data such as the remote sensor data 193 that vehicles record using their sensor sets. Vehicles that receive these V2X messages use this V2X data to improve their awareness of their environment. For vehicles that include Advanced Driver Assistance Systems (ADAS systems) or autonomous driving systems, the V2X data is inputted to these systems so that they can better understand their driving environment when providing their functionality.

An example of one specific type of sensor data includes GPS data. "GPS" refers to "geographic positioning system." The GPS data includes digital data that describes the geographic location of an object such as a vehicle or a smartphone.

An example of the V2X data according to some embodiments includes the V2X data 133 depicted in FIG. 1. For example, with reference to FIG. 1, the remote sensor data is received by the communication unit of the ego vehicle via a V2X transmission that includes V2X data including the remote sensor data as its payload; the medic system of the ego vehicle then parses the remote sensor data from the V2X data and stores the V2X data and the remote sensor data in the memory 127 of the ego vehicle 123.

In some embodiments, the V2X data includes the member data for the vehicular micro cloud. In this way, members of a vehicular micro cloud share sensor data and member data with one another. The member data describes, among other things, which tasks are assigned to which member of the vehicular micro cloud. The member data is described in more detail below.

Vehicular Micro Clouds

The embodiments described herein include a plurality of vehicular micro clouds. For example, the ego vehicle and the remote vehicle are connected vehicles (e.g., vehicles that include a processor, a communication unit, and an instance of the medic system) and members of one or more of a plurality of vehicular micro clouds. In some embodiments, the vehicular micro cloud hosts the medic system in a distributed fashion using the computing resources of the vehicles that are members of the vehicular micro cloud so that a cloud server and/or an edge server is not strictly necessary to provide the service of the medic system to the users of the medic system.

In some embodiments, a server such as a cloud server and/or an edge server is also an element of the vehicle micro cloud. A cloud server includes a conventional hardware server having network communication capabilities such as a computer, a laptop, a microcomputer, etc. An example of a cloud server according to some embodiments includes a cloud server 103 as depicted in FIG. 1. An edge server includes a conventional hardware server having network communication capabilities such as a computer, a laptop, a microcomputer, etc. An example of an edge server according to some embodiments includes an edge server 198 as depicted in FIG. 1.

In some embodiments, a vehicular micro cloud includes a group of connected vehicles where vehicles perform task(s) cooperatively/collaboratively. Vehicular micro clouds can be divided into two categories based on their mobility: (1) stationary; and (2) mobile. An example of a vehicular micro cloud according to some embodiments includes a vehicular micro cloud 194 depicted in FIG. 1. As depicted in FIG. 1, an operating environment 100 for the medic system 199 includes a plurality of vehicular micro clouds 194.

In the stationary cloud, a certain geographical region is designated as the vehicular micro cloud region, and vehicles entering that region contribute their resources for vehicular cloud services. A stationary vehicular micro cloud is sometimes referred to as a "static" vehicular micro cloud.

In the mobile vehicular cloud, on the other hand, the vehicular micro cloud moves as the micro cloud members move. A mobile vehicular micro cloud is sometimes referred to as a "dynamic" vehicular micro cloud.

In some embodiments, as an optional operating environment, the medic system is hosted by a plurality of members of a vehicular micro cloud. In some embodiments, these members are also registered with the medic system. For example, for each member the medic system has access to digital data that includes a unique identifier of the member. In some embodiments, each instance of digital data shared among the members of the vehicular micro cloud include one or more bits of data that include this unique identifier so that attribution of the digital data is provided; this attribution is beneficial to monitor and improve the functionality of the medic system as well as identify malicious users.

In some embodiments, the medic system causes the vehicles, which each include an instance of the medic system or at least a subset of the code and routines of the medic system, to execute steps to form the vehicular micro cloud.

Member data includes digital data that describes information about a vehicular micro cloud and its members. For example, the member data is digital data that describes the identity of the members of the vehicular micro cloud and their specific computing resources; all members of the vehicular micro cloud make their computing resources available to one another for their collective benefit. An example of the member data according to some embodiments includes the member data 171 depicted in FIG. 1.

In some embodiments, the medic system 199 cause the communication unit to transmit a wireless message to candidates for membership in the vehicular micro cloud that causes these candidates to join the vehicular micro cloud. The list of candidates is determined by the medic system based on the technical data which is transmitted by the candidates to one another via BSMs; in some embodiments, these BSMs also include sensor data recorded by the vehicles that transmit the BSMs.

In some embodiments, the medic system 199 for a hub of a specific vehicular micro cloud determines candidates to join the vehicular micro cloud managed by the hub as new vehicles come within V2X communication range of the hub (e.g., within 1,500 feet or some other transmission range included with V2X communication).

In some embodiments, when a new vehicle joins the vehicular micro cloud managed by the hub, the hub generates new member data for the vehicular micro cloud including, among other things, digital data describing the schedule of tasks which includes those tasks assigned to the new member. The hub then transmits V2X messages to the members of the vehicular micro cloud that includes V2X data that distributes the new member data to the members of the vehicular micro cloud, including the new member. The medic system for the new member is now responsible for executing the tasks assigned to it by the hub as described in the member data.

As briefly introduced above, vehicular micro clouds provide vehicular micro cloud tasks. A vehicular micro cloud task includes any task executed by a vehicular micro cloud or a group of vehicular micro clouds. As used herein, the terms "task" and "vehicular micro cloud task" refer to the same thing. A "sub-task" as used herein is a portion of a task or vehicular micro cloud task. An example of a task includes, for example, executing a computing process that is an element of delivering a vehicular cloud service to one or more members of the vehicular micro cloud.

In some embodiments, the member data describes, for each member of a particular vehicular micro cloud, the tasks assigned to each member. The member data also describes a schedule of tasks for the vehicular micro cloud. A schedule of tasks described by the member data 171 includes, for one or more vehicular micro clouds, digital data that describes one or more of the following: (1) what tasks are assigned; (2) for each assigned task, which member it is assigned to; and (3) for each assigned task, time(s) when the task is to be started and/or completed. In some embodiments, the members of a vehicular micro cloud exchange V2X messages and the V2X data includes, among other types of digital data, the member data.

In some embodiments, the vehicular micro cloud assigned by the hub of a micro cloud includes some or all of the tasks which are necessary to provide one or more vehicular cloud services. In some embodiments, the medic system is operable to receive member data for a plurality of vehicular micro clouds and organize a schedule of tasks for the members of the plurality of vehicular micro clouds that is operable to ensure that the plurality of vehicular cloud services provided by the plurality of vehicular micro clouds is uninterrupted even as members are entering and leaving different vehicular micro clouds.

In some embodiments, a vehicular micro cloud includes a group of connected vehicles that communicate with one another via V2X messages to provide, among other things such as a vehicular cloud service, the service of the medic system to the ego vehicle and/or the members of the vehicular micro cloud.

The vehicular micro cloud includes multiple members. A member of the vehicular micro cloud includes a connected vehicle that sends and receives V2X messages via a network (e.g., the network 105 depicted in FIG. 1). In some embodiments, the network is a serverless ad-hock vehicular network. In some embodiments, the members of the network are nodes of the serverless ad-hoc vehicular network.

In some embodiments, a serverless ad-hoc vehicular network is "serverless" because the serverless ad-hoc vehicular network does not include a server. In some embodiments, a serverless ad-hoc vehicular network is "ad-hoc" because the serverless ad-hoc vehicular network is formed its members when it is determined by one or more of the members to be needed or necessary. In some embodiments, a serverless ad-hoc vehicular network is "vehicular" because the serverless ad-hoc vehicular network only includes connected vehicles as its endpoints. In some embodiments, the term "network" refers to a V2V network.

In some embodiments, one or more members of the vehicular micro cloud host their own instances of the MSPF system 138. For example, the vehicular micro cloud includes a roadside unit that includes an edge server 198 that hosts the MSPF system 138.

In some embodiments, one or more members of the vehicular micro cloud are ambulatory service providers that are eligible to route an intercept course with the ego vehicle to provide medical services to the occupant of the ego vehicle that is experiencing a medical condition or symptoms of a medical condition. For example, the vehicular micro cloud includes an ambulance or a mobile medical service provider that is a member of the vehicular micro cloud.

In some embodiments, the ego vehicle and an ambulance that are members of a vehicular micro cloud communicate with one another via the vehicular micro cloud to communicate their respective locations and to computationally collaborate with one another to determine intersecting routes for each of them to travel so that the occupant of the ego vehicle is able to receive medical service from the ambulance or a medical service provider that is an occupant of the ambulance.

In some embodiments, the vehicular micro cloud only includes vehicles. For example, the serverless ad-hoc network does not include the following: an infrastructure device, a base station, a roadway device, an edge server, an edge node, and a cloud server. An infrastructure device includes any hardware infrastructure device in a roadway environment such as a traffic signal, traffic light, traffic sign, or any other hardware device that has or does not have the ability to wirelessly communicate with a wireless network. In some embodiments, the edge server 198 depicted in FIG. 1 is an element of a hardware infrastructure device.

In some embodiments, the serverless ad-hoc vehicular network includes a set of sensor rich vehicles. A sensor rich vehicle is a connected vehicle that includes a rich sensor set.

In some embodiments, one or more of the ego vehicle and the remote vehicle depicted in FIG. 1 are examples of a sensor rich vehicle. Although only one remote vehicle is depicted in FIG. 1, in practice the operating environment may include one or more remote vehicles.

In some embodiments, an operating environment that includes the serverless ad-hoc vehicular network also includes a legacy vehicle. A legacy vehicle is a connected vehicle that includes a legacy sensor set. The overall sensing ability of the rich sensor set is greater than the overall sensing ability of the legacy sensor set. For example, a roadway environment includes a set of sensor rich vehicles and a legacy vehicle; the rich sensor set is operable to generate sensor measurements that more accurately describe the geographic locations of objects in the roadway environment when compared to the sensor measurements generated by the legacy sensor set.

In some embodiments, the legacy vehicle is an element of the serverless ad-hoc vehicular network. In some embodiments, the legacy vehicle is not an element of the serverless ad-hoc vehicular network but is able to provide shared rides to users because the driver of the legacy vehicle has a smart device (e.g., an electronic processor-based computing device such as a smartphone, smartwatch, tablet computer, laptop, smart glasses, etc.) which they use to receive information that enables them to participate as registered vehicles that provide shared rides to the users of the Service provided by the medic system.

In some embodiments, the serverless ad-hoc vehicular network is a vehicular micro cloud. It is not a requirement of the embodiments described herein that the serverless ad-hoc vehicular network is a vehicular micro cloud. Accordingly, in some embodiments the serverless ad-hoc vehicular network is not a vehicular micro cloud.

In some embodiments, the serverless ad-hoc vehicular network includes a similar structure that is operable to provide some or all of the functionality as a vehicular micro cloud. Accordingly, a vehicular micro cloud is now described according to some embodiments to provide an understanding of the structure and functionality of the serverless ad-hoc vehicular network according to some embodiments. When describing the vehicular micro cloud, the term "vehicular micro cloud" can be replaced by the term "group of connected vehicles" since a vehicular micro cloud is an example of a group of connected vehicles in some embodiments.

Distributed data storage and computing by a group of connected vehicles (i.e., a "vehicular micro cloud") is a promising solution to cope with an increasing network traffic generated for and by connected vehicles. Vehicles collaboratively store (or cache) data sets in their onboard data storage devices and compute and share these data sets over vehicle-to-vehicle (V2V) networks as requested by other vehicles. Using vehicular micro clouds removes the need for connected vehicles to access remote cloud servers or edge servers by vehicle-to-network (V2N) communications (e.g., by cellular networks) whenever they need to get access to unused computing resources such as shared data (e.g., some or all of the system data 129 described herein), shared computational power, shared bandwidth, shared memory, and cloudification services.

Example Vehicular Micro Cloud Tasks

Examples of vehicular micro cloud tasks (herein, "tasks") are now described according to some embodiments. Vehicular micro clouds are motivated by the emerging concept of "vehicle cloudification." Vehicle cloudification means that vehicles equipped with on-board computer unit(s) and wireless communication functionalities form a cluster, called a vehicular micro cloud, and collaborate with other members of the vehicular micro cloud over V2V networks or V2X networks to perform computation, data storage, and data communication tasks in an efficient way. These types of tasks are referred to herein as "vehicular micro cloud tasks" or "tasks" if plural, or a "vehicular micro cloud task" or "task" if singular.

In some embodiments, a vehicular micro cloud task includes any computational, data storage, or data communication task collaboratively performed by a plurality of the members of a vehicular micro cloud. In some embodiments, the set of tasks described above with regards to the example general method include one or more vehicular micro cloud tasks as described herein.

In some embodiments, a computational task includes a processor executing code and routines to output a result. The result includes digital data that describes the output of executing the code and routines. For example, a computational task includes a processor executing code and routines to identify a problem (e.g., a collision whose likelihood satisfies a threshold of probability described by the threshold data), and the result includes digital data that describes the solution to the problem (e.g., a series of driving maneuvers that will avoid a collision or make the likelihood of collision no longer satisfy the threshold). In some embodiments, the computational task is broken down into sub-tasks whose completion is equivalent to completion of the computational task. In this way, the processors of a plurality of micro cloud members are assigned different sub-tasks configured to complete the computational task; the micro cloud members take steps to complete the sub-tasks in parallel and share the result of the completion of the sub-task with one another via V2X wireless communication. In this way, the plurality of micro cloud members work together collaboratively to complete the computational task. The processors include, for example, the onboard units or electronic control units (ECUs) of a plurality of connected vehicles that are micro cloud members.

In some embodiments, the computational task includes identifying the medical condition that an occupant is experiencing based on the cabin data. In some embodiments, the computational task includes identifying the remedial action plan that is appropriate for the identified medical condition. In some embodiments, the computational task includes executing one or more digital twin simulations (e.g., to identify a remedial action plan for different combinations of medical conditions and roadway conditions). In some embodiments, the computational task includes calculating intercept courses between the ego vehicle and a remote medical service provider to assist the occupant of the ego vehicle that is experiencing a medical condition. These examples are illustrative. Other examples are possible.

In some embodiments, the ego vehicle and an ambulance (or some other mobile medical service provider) are members of a vehicular micro cloud. These members communicate with one another via the vehicular micro cloud to communicate their respective locations. In some embodiments, one or more members of the vehicular micro cloud computationally collaborate with one another to determine intersecting routes for each of the ego vehicle and the ambulance to travel so that the occupant of the ego vehicle is able to receive medical service from the ambulance or a medical service provider that is an occupant of the ambulance. These intersecting routes may be determined at least in part on one or more digital twin simulations and the existing roadway conditions observed by the members of the vehicular micro cloud. In some embodiments, the output of this process is route data that describes the intercepting routes for each of the ego vehicle and the ambulance. In some embodiments, the vehicular micro cloud communicates the route data for each of the ambulance and the ego vehicle via one or more V2X messages.

In some embodiments, a data storage task includes a processor storing digital data in a memory of a connected vehicle. For example, a digital data file which is too big to be stored in the memory of any one vehicle is stored in the memory of multiple vehicles. In some embodiments, the data storage task is broken down into sub-tasks whose completion is equivalent to completion of the data storage task. In this way, the processors of a plurality of micro cloud members are assigned different sub-tasks configured to complete the data storage task; the micro cloud members take steps to complete the sub-tasks in parallel and share the result of the completion of the sub-task with one another via V2X wireless communication. In this way, the plurality of micro cloud members work together collaboratively to complete the data storage task. For example, a sub-task for a data storage task includes storing a portion of a digital data file in a memory of a micro cloud member; other micro cloud members are assigned sub-tasks to store the remaining portions of digital data file in their memories so that collectively the entire file is stored across the vehicular micro cloud or a sub-set of the vehicular micro cloud.

In some embodiments, a data communication task includes a processor using some or all of the network bandwidth available to the processor (e.g., via the communication unit of the connected vehicle) to transmit a portion a V2X wireless message to another endpoint. For example, a V2X wireless message includes a payload whose file size is too big to be transmitted using the bandwidth available to any one vehicle and so the payload is broken into segments and transmitted at the same time (or contemporaneously) via multiple wireless messages by multiple micro cloud members. In some embodiments, the data communication task is broken down into sub-tasks whose completion is equivalent to completion of the data storage task. In this way, the processors of a plurality of micro cloud members are assigned different sub-tasks configured to complete the data storage task; the micro cloud members take steps to complete the sub-tasks in parallel and share the result of the completion of the sub-task with one another via V2X wireless communication. In this way, the plurality of micro cloud members work together collaboratively to complete the data storage task. For example, a sub-task for a data communication task includes transmitting a portion of a payload for a V2X message to a designated endpoint; other micro cloud members are assigned sub-tasks to transmit the remaining portions of payload using their available bandwidth so that collectively the entire payload is transmitted.

In some embodiments, a vehicular micro cloud task includes determining a series of driving maneuvers (a "driving plan") for operating the ego vehicle in various circumstances considering the combination of different variables such as weather conditions, lighting conditions, road-surface conditions (e.g., wet or icy conditions), roadway congestion (e.g., number of vehicles per unit of measurement such as feet or meters), and road geometry conditions.

In some embodiments, a vehicular micro cloud task is collaboratively performed by the plurality of members executing computing processes in parallel which are configured to complete the execution of the vehicular micro cloud task.

In some embodiments, a vehicular micro cloud includes a plurality of members that execute computing processes whose completion results in the execution of a vehicular micro cloud task. For example, the serverless ad-hoc vehicular network provides a vehicular micro cloud task to a legacy vehicle.

Vehicular micro clouds are beneficial, for example, because they help vehicles to perform computationally expensive tasks (e.g., determining the analysis data, executing the digital twin simulations, etc.) that they could not perform alone or store large data sets that they could not store alone. In some embodiments, the computational power of a solitary ego vehicle is sufficient to execute these tasks.

Vehicular micro clouds are described in the patent applications that are incorporated by reference in this paragraph. This patent application is related to the following patent applications, the entirety of each of which is incorporated herein by reference: U.S. patent application Ser. No. 16/943,443 filed on Jul. 30, 2020 and entitled "Vehicular Nano Cloud"; U.S. Pat. No. 10,924,337 issued on Feb. 16, 2021 and entitled "Vehicular Cloud Slicing"; U.S. patent application Ser. No. 15/358,567 filed on Nov. 22, 2016 and entitled "Storage Service for Mobile Nodes in a Roadway Area"; U.S. patent application Ser. No. 15/799,442 filed on Oct. 31, 2017 and entitled "Service Discovery and Provisioning for a Macro-Vehicular Cloud"; U.S. patent application Ser. No. 15/845,945 filed on Dec. 18, 2017 and entitled "Managed Selection of a Geographical Location for a Micro-Vehicular Cloud"; U.S. patent application Ser. No. 15/799,963 filed on Oct. 31, 2017 and entitled "Identifying a Geographic Location for a Stationary Micro-Vehicular Cloud"; U.S. patent application Ser. No. 16/443,087 filed on Jun. 17, 2019 and entitled "Cooperative Parking Space Search by a Vehicular Micro Cloud"; U.S. patent application Ser. No. 16/739,949 filed on Jan. 10, 2020 and entitled "Vehicular Micro Clouds for On-demand Vehicle Queue Analysis"; U.S. patent application Ser. No. 16/735,612 filed on Jan. 6, 2020 and entitled "Vehicular Micro Cloud Hubs"; U.S. patent application Ser. No. 16/387,518 filed on Apr. 17, 2019 and entitled "Reorganizing Autonomous Entities for Improved Vehicular Micro Cloud Operation"; U.S. patent application Ser. No. 16/273,134 filed on Feb. 11, 2019 and entitled "Anomaly Mapping by Vehicular Micro Clouds"; U.S. patent application Ser. No. 16/246,334 filed on Jan. 11, 2019 and entitled "On-demand Formation of Stationary Vehicular Micro Clouds"; and U.S. patent application Ser. No. 16/200,578 filed on Nov. 26, 2018 and entitled "Mobility-oriented Data Replication in a Vehicular Micro Cloud."

Nano clouds are described in more detail below, as well as in U.S. patent application Ser. No. 16/943,443 filed on Jul. 30, 2020 and entitled "Vehicular Nano Cloud," the entirety of which is incorporated herein by reference. Vehicular micro cloud slices are described in more detail in U.S. Pat. No. 10,924,337 issued on Feb. 16, 2021 and entitled "Vehicular Cloud Slicing," the entirety of which is incorporated herein by reference.

In some embodiments, the medic system is operable to execute a set of tasks assigned by a vehicular micro cloud.

The endpoints that are part of the vehicular micro cloud may be referred to herein as "members," "micro cloud members," or "member vehicles." Examples of members include one or more of the following: a connected vehicle; an edge server; a cloud server; any other connected device that has computing resources and has been invited to join the vehicular micro cloud by a handshake process. In some embodiments, the term "member vehicle" specifically refers to only connected vehicles that are members of the vehicular micro cloud whereas the terms "members" or "micro cloud members" is a broader term that may refer to one or more of the following: endpoints that are vehicles; and endpoints that are not vehicles such as roadside units.

As used herein, the term "sensor data" refers to one or more of the ego sensor data, the remote sensor data, or a combination of the ego data and the remote sensor data.

The medical service provider 108 is a human that is trained to provide a medical service to treat a medical condition or a set of symptoms of the occupant of the ego vehicle 123 that is experiencing the medical condition or the set of symptoms. In some embodiments, the medical service provider 108 is an occupant of a remote vehicle 124 (e.g., an ambulance or some other mobile medical service provider) that meets the ego vehicle 123 on the roadway to provide the medical service to the occupant of the ego vehicle 123.

The driver 109 is a human driver of the ego vehicle 123. In some embodiments, the driver 109 is the occupant of the ego vehicle 123 that is experiencing the medical condition.

In some embodiments, the V2X data 133 is received by the ego vehicle 123 because the ego vehicle 123 and the remote vehicle 124 are members of the same vehicular micro cloud 194.

Threshold data includes digital data that describes any threshold described herein. An example of the threshold data includes the threshold data 196 depicted in FIG. 1.

A vehicle control system is an onboard system of a vehicle that controls the operation of a functionality of the vehicle. ADAS systems and autonomous driving systems are examples of vehicle control systems. Examples of the vehicle control system according to some embodiments includes the vehicle control system 153 depicted in FIGS. 1 and 2 and the autonomous driving system 152 depicted in FIG. 2.

Example General Method

In some embodiments, the medic system includes code and routines that are operable, when executed by a processor, to cause the processor to execute one or more steps of an example general method described herein. The medic system may be an element of one or more of the following: an ego vehicle; a remote connected vehicle; a cloud server; and an edge server installed in a roadway device such as a roadside unit (RSU). As described, the medic system is an element of the ego vehicle, but this description is not intended to be limiting.

In some embodiments, these steps are executed by a processor or onboard vehicle computer of an ego vehicle. The ego vehicle is a connected vehicle. A connected vehicle is a vehicle that includes a communication unit. An example of a communication unit includes the communication unit 145 depicted in FIG. 1. The remote connected vehicle is also a connected vehicle, and so, it includes a communication unit.

As used herein, the term "wireless message" refers to a V2X message transmitted by a communication unit of a connected vehicle such as a remote connected vehicle or the ego vehicle.

The example general method is now described. In some embodiments, one or more steps of the example general method are skipped or modified. The steps of the example general method may be executed in any order, and not necessarily the order presented.

In some embodiments, a plurality of vehicles on a roadway include instances of the medic system and the medic systems of these vehicles also execute some or all of the steps described below. For example, one or more of these steps are executed by the members of a vehicular micro cloud in some embodiments. In some embodiments, a server such as a cloud server or an edge server includes an instance of the medic system, and one or more steps are executed by the medic system of one or more of these entities.

The steps of the example general method are now described according to some embodiments.

Step 1: The medic system causes the sensor set of the ego vehicle to record ego sensor data. The ego sensor data includes digital data that describes the sensor measurements of the sensors that are included in the sensor set of the ego vehicle. In some embodiments, the individual sensor measurements are time stamped so an instance of ego sensor data describes both a sensor measurement and when this measurement was recorded. In some embodiments, the ego sensor data includes time data that describes the timestamps for the sensor measurements.

In some embodiments, the sensor measurements described by the ego sensor data describe one or more of the following types of roadway data 154: the ego vehicle over time including its location in a roadway environment over time; the location of the ego vehicle relative to other objects within the roadway environment over time; the driver's operation of the ego vehicle over time, the presence of other objects over time within the roadway environment that includes the ego vehicle; the location of these objects in the roadway over time relative to other objects (e.g., the location of these other objects relative to one another and relative to the ego vehicle); the behavior of these other objects over time; the geometry of the roadway over time; features in the roadway over time and changes in one or more of their position, velocity, and acceleration; kinematic information about the ego vehicle and/or any objects in the roadway environment; and any aspect of the roadway environment that is measurable by the sensors included in the sensor set of the ego vehicle.

An example of the ego sensor data according to some embodiments includes the ego sensor data 195 depicted in FIG. 1. The sensors included in the sensor set, and the type of measurements they can record, are described in more detail below.

In some embodiments, the ego sensor data 195 includes the cabin data 155 described above. The cabin data 155 includes digital data describing any sensor measurements recorded by the cabin sensors 150.

Step 2: (Optional) A set of one or more remote vehicles in sensor range of the ego vehicle include their own instance of the medic system. The medic system of these remote vehicles causes the sensor sets of these remote vehicles to record sensor measurements of their roadway environment. These sensor measurements include sensor measurements similar to those described above for the roadway data 154.

The sensor measurements recorded by an individual remote connected vehicle from the set of remote vehicles is described by remote sensor data. The remote sensor data includes digital data that describes the sensor measurements of the sensors that are included in the sensor set of the remote connected vehicle. In some embodiments, the individual sensor measurements are time stamped so an instance of remote sensor data describes both a sensor measurement and when this measurement was recorded. In some embodiments, the remote sensor data includes time data that describes the timestamps for the sensor measurements.

In some embodiments, the sensor measurements described by the remote sensor data describe one or more of the following: the remote connected vehicle over time including its location in a roadway environment over time; the location of the remote connected vehicle relative to other objects within the roadway environment over time; a driver's operation of the remote connected vehicle over time, the presence of other objects (including the presence of the ego vehicle) over time within the roadway environment that includes the remote connected vehicle; the location of these objects (including the location of the ego vehicle) in the roadway over time relative to other objects (e.g., the location of the ego vehicle relative to the remote connected vehicle as measured from the perspective of the remote connected vehicle); the behavior of these other objects (including the behavior of the ego vehicle) over time; the geometry of the roadway over time; features in the roadway over time and changes in one or more of their position, velocity, and acceleration; kinematic information about the remote vehicle and/or any objects in the roadway environment; and any aspect of the roadway environment that is measurable by the sensors included in the sensor set of the remote vehicle The sensors included in the sensor sets of the remote vehicles are similar to those included in the ego vehicle.

Step 3: (Optional) In some embodiments, the ego vehicle and the set of remote vehicles described in step 2 are members of a vehicular micro cloud. In some embodiments, the vehicular micro cloud is included in a plurality vehicular micro clouds. In some embodiments, the ego vehicle and the remote vehicles are members of different vehicular micro clouds included in the plurality.

Step 4: The medic system of the ego vehicle is executed by a processor of the ego vehicle. The medic system, when executed by the processor, causes the processor to determine that a driver of the ego vehicle (or some other occupant of the ego vehicle) is experiencing a debilitating medical condition based, for example, on a comparison of the of the cabin data to the medical conditions data.

Step 5: The vehicle control system of the ego vehicle includes a protocol that is operable to decrease the autonomy level of the ego vehicle responsive to the attentiveness of the driver of the ego vehicle not satisfying a threshold for attentiveness described by the threshold data. For example, the vehicle control system randomly checks the eye gaze of the driver and the pressure on the steering wheel to ensure that the driver is providing attention to the roadway and the driving interface of the vehicle compares this to a threshold for attentiveness to ensure that the drivers actions satisfy the threshold thereby indicating that the driver is "inattentive." However, application of this protocol is problematic and decreases safety on the roadway if the driver is experiencing a debilitating medical condition.

The medic system of the ego vehicle is executed by a processor of the ego vehicle. The medic system, when executed by the processor, causes the processor to override the protocol to decrease the autonomy level of the ego vehicle responsive to the inattentiveness of the driver to the driving interface of the ego vehicle so that the driver can be inattentive to the driver interface (e.g., while they are experiencing a debilitating medical condition) without the autonomy level of the ego vehicle being decreased.

Step 6: The medic system of the ego vehicle is executed by a processor of the ego vehicle. The medic system, when executed by the processor, causes the processor to modify an operation of the vehicle control system of the ego vehicle to increase the autonomy level of the ego vehicle to decrease a driving responsibility of the driver responsive to the debilitating medical condition which they are experiencing. In some embodiments, the reaction data specifies this step 6. In some embodiments, the reaction data specifies how much and in what ways to increase the autonomy level of the ego vehicle.

In some embodiments, the ego vehicle 123 is an autonomous vehicle or a semi-autonomous vehicle. For example, the ego vehicle 123 includes a set of Advanced Driver Assistance Systems (e.g., a set of vehicle control systems) which provide autonomous features to the ego vehicle 123 which are sufficient to render the ego vehicle 123 an autonomous vehicle. The vehicle control systems includes one or more ADAS systems. In some embodiments, an autonomous driving system includes a set of vehicle control systems that collectively or individually provide a set of autonomous driving features that are sufficient to render the ego vehicle a Level 3 autonomous vehicle or higher. An example of the autonomous driving system according to some embodiments includes the autonomous driving system 152 depicted in FIG. 2.

The National Highway Traffic Safety Administration ("NHTSA") has defined different "levels" of autonomous vehicles, e.g., Level 0, Level 1, Level 2, Level 3, Level 4, and Level 5. If an autonomous vehicle has a higher-level number than another autonomous vehicle (e.g., Level 3 is a higher-level number than Levels 2 or 1), then the autonomous vehicle with a higher-level number offers a greater combination and quantity of autonomous features relative to the vehicle with the lower-level number. The different levels of autonomous vehicles are described briefly below.

Level 0: The vehicle control systems installed in a vehicle have no vehicle control. The vehicle control systems may issue warnings to the driver of the vehicle. A vehicle which is Level 0 is not an autonomous or semi-autonomous vehicle.

Level 1: The driver must be ready to take driving control of the autonomous vehicle at any time. The vehicle control systems installed in the autonomous vehicle may provide autonomous features such as one or more of the following: Adaptive Cruise Control (ACC); and Parking Assistance with automated steering and Lane Keeping Assistance (LKA) Type II, in any combination.

Level 2: The driver is obliged to detect objects and events in the roadway environment and respond if the vehicle control systems installed in the autonomous vehicle fail to respond properly (based on the driver's subjective judgement). The vehicle control systems installed in the autonomous vehicle executes accelerating, braking, and steering. The vehicle control systems installed in the autonomous vehicle can deactivate immediately upon takeover by the driver.

Level 3: Within known, limited environments (such as freeways), the driver can safely turn their attention away from driving tasks but must still be prepared to take control of the autonomous vehicle when needed.

Level 4: The vehicle control systems installed in the autonomous vehicle can control the autonomous vehicle in all but a few environments such as severe weather. The driver must enable the automated system (which is comprised of the vehicle control systems installed in the vehicle) only when it is safe to do so. When the automated system is enabled, driver attention is not required for the autonomous vehicle to operate safely and consistent with accepted norms.

Level 5: Other than setting the destination and starting the system, no human intervention is required. The automated system can drive to any location where it is legal to drive and make its own decision (which may vary based on the jurisdiction where the vehicle is located).

A highly autonomous vehicle (HAV) is an autonomous vehicle that is Level 3 or higher.

Accordingly, in some embodiments the ego vehicle 123 is one of the following: a Level 1 autonomous vehicle; a Level 2 autonomous vehicle; a Level 3 autonomous vehicle; a Level 4 autonomous vehicle; a Level 5 autonomous vehicle; and an HAV.

In some embodiments, the vehicle control systems includes one or more of the following ADAS systems: an ACC system; an adaptive high beam system; an adaptive light control system; an automatic parking system; an automotive night vision system; a blind spot monitor; a collision avoidance system; a crosswind stabilization system; a driver drowsiness detection system; a driver monitoring system; an emergency driver assistance system; a forward collision warning system; an intersection assistance system; an intelligent speed adaption system; a lane departure warning system (also referred to as a LKA system); a pedestrian protection system; a traffic sign recognition system; a turning assistant; a wrong-way driving warning system; autopilot; sign recognition; and sign assist. Each of these example ADAS systems provide their own features and functionality that may be referred to herein as an "ADAS feature" or an "ADAS functionality," respectively. The features and functionality provided by these example ADAS systems are also referred to herein as an "autonomous feature" or an "autonomous functionality," respectively.

In some embodiments, reducing an autonomy level of the ego vehicle includes reducing a functionality or degree of driver assistance provided by one or more of the ADAS systems of the ego vehicle. In some embodiments, increasing an autonomy level of the ego vehicle includes increasing a functionality or degree of driver assistance provided by one or more of the ADAS systems of the ego vehicle. In some embodiments, the ego vehicle is sold with only a portion of the ADAS software and/or ADAS hardware enabled. This ADAS software and/or ADAS hardware can be enabled at a later date, for example, in exchange for a fee. In some embodiments, the medic system enables ADAS software and/or ADAS hardware responsive to detecting a medical condition in order to provide increased driving assistance to the driver of the ego vehicle while they are experiencing the medical condition. If all of the installed ADAS software and/or ADAS hardware is enabled, then this is referred to as "maximizing" the available autonomy level of the ego vehicle.

In some embodiments, system data includes some or all of the digital data described herein. In some embodiments, the communication unit of an ego vehicle includes a V2X radio. The V2X radio operates in compliance with a V2X protocol. In some embodiments, the V2X radio is a cellular-V2X radio ("C-V2X radio"). In some embodiments, the V2X radio broadcasts Basic Safety Messages ("BSM" or "safety message" if singular, "BSMs" or "safety messages" if plural). In some embodiments, the safety messages broadcast by the communication unit include some or all of the system data as its payload. In some embodiments, the system data is included in part 2 of the safety message as specified by the Dedicated Short-Range Communication (DSRC) protocol. In some embodiments, the payload includes digital data that describes, among other things, sensor data that describes a roadway environment that includes the members of the vehicular micro cloud.

As used herein, the term "vehicle" refers to a connected vehicle. For example, the ego vehicle and remote connected vehicle depicted in FIG. 1 are connected vehicles.

A connected vehicle is a conveyance, such as an automobile, which includes a communication unit that enables the conveyance to send and receive wireless messages via one or more vehicular networks. The embodiments described herein are beneficial for both drivers of human-driven vehicles as well as the autonomous driving systems of autonomous vehicles. For example, the medic system improves the performance of a vehicle control system, which benefits the performance of the vehicle itself by enabling it to operate more safety or in a manner that is more satisfactory to a human driver of the ego vehicle.

In some embodiments, the medic system is software installed in an onboard unit (e.g., an electronic control unit (ECU)) of a vehicle having V2X communication capability. The vehicle is a connected vehicle and operates in a roadway environment with N number of remote vehicles that are also connected vehicles, where N is any positive whole number that is sufficient to satisfy a threshold for forming a vehicular micro cloud. The roadway environment may include one or more of the following example elements: an ego vehicle; N remote vehicles; a cloud server; and an edge server. The edge server may be an element of a roadside unit. For the purpose of clarity, the N remote vehicles may be referred to herein as the "remote connected vehicle" or the "remote vehicles" and this will be understood to describe N remote vehicles.

In some embodiments, the medic system includes code and routines stored on and executed by a cloud server or an edge server.

The ego vehicle and the remote vehicles may be human-driven vehicles, autonomous vehicles, or a combination of human-driven vehicles and autonomous vehicles. In some embodiments, the ego vehicle and the remote vehicles may be equipped with DSRC equipment such as a GPS unit that has lane-level accuracy and a DSRC radio that is capable of transmitting DSRC messages.

Nano Clouds

In some embodiments, the ego vehicle and some or all of the remote vehicles include their own instance of a medic system. For example, in addition to the ego vehicle, some or all of the remote vehicles include an onboard unit having an instance of the medic system installed therein.

In some embodiments, the ego vehicle and one or more of the remote vehicles are members of a vehicular micro cloud. In some embodiments, the ego vehicle and some, but not all, of the remote vehicles are members of the vehicular micro cloud. In some embodiments, the ego vehicle and some or all of the remote vehicles are members of the same vehicular macro cloud but not the same vehicular micro cloud, meaning that they are members of various vehicular micro clouds that are all members of the same vehicular macro cloud so that they are still interrelated to one another by the vehicular macro cloud. An example of a vehicular micro cloud according to some embodiments includes the vehicular micro cloud 194 depicted in FIG. 1.

In some embodiments multiple instances of the medic system are installed in a group of connected vehicles. In some embodiments, the group of connected vehicles are arranged as a vehicular micro cloud. As described in more detail below, the medic system further organizes the vehicular micro cloud into a set of nano clouds which are each assigned responsibility for completion of a sub-task. Each nano cloud includes at least one member of the vehicular micro cloud so that each nano cloud is operable to complete assigned sub-tasks of a vehicular micro cloud task for the benefit of the members of the vehicular micro cloud.

In some embodiments, a nano cloud includes a subset of a vehicular micro cloud that is organized within the vehicular micro cloud as an entity managed by a hub wherein the entity is organized for the purpose of a completing one or more sub-tasks of a vehicular micro cloud task.

Hub or Hub Vehicle

Vehicular micro clouds are managed by a hub or hub vehicle. In some embodiments, the medic system that executes a method as described herein (e.g., the method 300 depicted in FIG. 3, the method 400 depicted in FIGS. 4A, 4C, 4D, 4E, and 4F, or the example general method described herein, etc.) is an element of a hub or a hub vehicle. For example, the vehicular micro cloud formed by the medic system includes a hub vehicle that provides the following example functionality in addition to the functionality of the methods described herein: (1) controlling when the set of member vehicles leave the vehicular micro cloud (i.e., managing the membership of the vehicular micro cloud, such as who can join, when they can join, when they can leave, etc.); (2) determining how to use the pool of vehicular computing resources to complete a set of tasks in an order for the set of member vehicles wherein the order is determined based on a set of factors that includes safety; (3) determining how to use the pool of vehicular computing resources to complete a set of tasks that do not include any tasks that benefit the hub vehicle; and determining when no more tasks need to be completed, or when no other member vehicles are present except for the hub vehicle, and taking steps to dissolve the vehicular micro cloud responsive to such determinations.

The "hub vehicle" may be referred to herein as the "hub." An example of a hub vehicle according to some embodiments includes the ego vehicle 123 depicted in FIG. 1. In some embodiments, the operating environment 100 includes a roadside unit or some other roadway device, and this roadway device is the hub of the vehicular micro cloud.

In some embodiments, the medic system determines which member vehicle from a group of vehicles (e.g., the ego vehicle and one or more remote vehicles) will serve as the hub vehicle based on a set of factors that indicate which vehicle (e.g., the ego vehicle or one of the remote vehicles) is the most technologically sophisticated. For example, the member vehicle that has the fastest onboard computer may be the hub vehicle. Other factors that may qualify a vehicle to be the hub include one or more of the following: having the most accurate sensors relative to the other members; having the most bandwidth relative to the other members; and having the most unused memory relative to the other members. Accordingly, the designation of which vehicle is the hub vehicle may be based on a set of factors that includes which vehicle has: (1) the fastest onboard computer relative to the other members; (2) the most accurate sensors relative to the other members; (3) the most bandwidth relative to the other members or other network factors such having radios compliant with the most modern network protocols; and (4) most available memory relative to the other members.

In some embodiments, the designation of which vehicle is the hub vehicle changes over time if the medic system determines that a more technologically sophisticated vehicle joins the vehicular micro cloud. Accordingly, the designation of which vehicle is the hub vehicle is dynamic and not static. In other words, in some embodiments the designation of which vehicle from a group of vehicles is the hub vehicle for that group changes on the fly if a "better" hub vehicle joins the vehicular micro cloud. The factors described in the preceding paragraph are used to determine whether a new vehicle would be better relative to the existing hub vehicle.

In some embodiments, the hub vehicle includes a memory that stores technical data. The technical data includes digital data describing the technological capabilities of each vehicle included in the vehicular micro cloud. The hub vehicle also has access to each vehicle's sensor data because these vehicles broadcast V2X messages that include the sensor data as the payload for the V2X messages. An example of such V2X messages include Basic Safety Messages (BSMs) which include such sensor data in part 2 of their payload. In some embodiments, the technical data is included in the member data (and/or sensor data) depicted in FIG. 1 which vehicles such as the ego vehicle 123 and the remote vehicle 124 broadcast to one another via BSMs. In some embodiments, the member data also includes the sensor data of the vehicle that transmits the BSM as well as some or all of the other digital data described herein as being an element of the member data.

In some embodiments, the technical data is an element of the sensor data (e.g., the ego sensor data or the remote sensor data) which is included in the V2X data.

A vehicle's sensor data is the digital data recorded by that vehicle's onboard sensor set 126. In some embodiments, an ego vehicle's sensor data includes the sensor data recorded by another vehicle's sensor set 126; in these embodiments, the other vehicle transmits the sensor data to the ego vehicle via a V2X communication such as a BSM or some other V2X communication.

In some embodiments, the technical data is an element of the sensor data. In some embodiments, the vehicles distribute their sensor data by transmitting BSMs that includes the sensor data in its payload and this sensor data includes the technical data for each vehicle that transmits a BSM; in this way, the hub vehicle receives the technical data for each of the vehicles included in the vehicular micro cloud.

In some embodiments, the hub vehicle is whichever member vehicle of a vehicular micro cloud has a fastest onboard computer relative to the other member vehicles.

In some embodiments, the medic system is operable to provide its functionality to operating environments and network architectures that do not include a server. Use of servers is problematic in some scenarios because they create latency. For example, some prior art systems require that groups of vehicles relay all their messages to one another through a server. By comparison, the use of server is an optional feature for the medic system. For example, the medic system is an element of a roadside unit that includes a communication unit 145 but not a server. In another example, the medic system is an element of another vehicle such as one of the remote vehicles 124.

In some embodiments, the operating environment of the medic system includes servers. Optionally, in these embodiments the medic system includes code and routines that predict the expected latency of V2X communications involving serves and then time the transmission of these V2X communications so that the latency is minimized or reduced.

In some embodiments, the medic system is operable to provide its functionality even though the vehicle which includes the medic system does not have a Wi-Fi antenna as part of its communication unit. By comparison, some of the existing solutions require the use of a Wi-Fi antenna in order to provide their functionality. Because the medic system does not require a Wi-Fi antenna in some embodiments, the medic system is able to provide its functionality to more vehicles, including older vehicles without Wi-Fi antennas.

In some embodiments, the medic system includes code and routines that, when executed by a processor, cause the processor to control when a member of the vehicular micro cloud may leave or exit the vehicular micro cloud. This approach is beneficial because it means the hub vehicle has certainty about how much computing resources it has at any given time since it controls when vehicles (and their computing resources) may leave the vehicular micro cloud. The existing solutions do not provide this functionality.

In some embodiments, the medic system includes code and routines that, when executed by a processor, cause the processor to designate a particular vehicle to serve as a hub vehicle responsive to determining that the particular vehicle has sufficient unused computing resources and/or trustworthiness to provide micro cloud services to a vehicular micro cloud using the unused computing resources of the particular vehicle. This is beneficial because it guarantees that only those vehicles having something to contribute to the members of the vehicular micro cloud may join the vehicular micro cloud. In some embodiments, vehicles which the medic system determines are ineligible to participate as members of the vehicular micro cloud are also excluded from providing rides to users as part of the Service.

In some embodiments, the medic system manages the vehicular micro cloud so that it is accessible for membership by vehicles which do not have V2V communication capability. This is beneficial because it ensures that legacy vehicles have access to the benefits provided by the vehicular micro cloud. The existing approaches to task completion by a plurality of vehicles do not provide this functionality.

In some embodiments, the medic system is configured so that a particular vehicle (e.g., the ego vehicle) is pre-designated by a vehicle manufacturer to serve as a hub vehicle for any vehicular micro cloud that it joins. The existing approaches to task completion by a plurality of vehicles do not provide this functionality.

The existing solutions generally do not include vehicular micro clouds. Some groups of vehicles (e.g., cliques, platoons, etc.) might appear to be a vehicular micro cloud when they in fact are not a vehicular micro cloud. For example, in some embodiments a vehicular micro cloud requires that all its members share it unused computing resources with the other members of the vehicular micro cloud. Any group of vehicles that does not require all its members to share their unused computing resources with the other members is not a vehicular micro cloud.

In some embodiments, a vehicular micro cloud does not require a server and preferably would not include one because of the latency created by communication with a server. Accordingly, in some but not all embodiments, any group of vehicles that includes a server or whose functionality incorporates a server is not a vehicular micro cloud as this term is used herein.

In some embodiments, a vehicular micro cloud formed by a medic system is operable to harness the unused computing resources of many different vehicles to perform complex computational tasks that a single vehicle alone cannot perform due to the computational limitations of a vehicle's onboard vehicle computer which are known to be limited. Accordingly, any group of vehicles that does harness the unused computing resources of many different vehicles to perform complex computational tasks that a single vehicle alone cannot perform is not a vehicular micro cloud.

In some embodiments, a vehicular micro cloud can include vehicles that are parked, vehicles that are traveling in different directions, infrastructure devices, or almost any endpoint that is within communication range of a member of the vehicular micro cloud.

In some embodiments, the medic system is configured so that vehicles are required to have a predetermined threshold of unused computing resources to become members of a vehicular micro cloud. Accordingly, any group of vehicles that does not require vehicles to have a predetermined threshold of unused computing resources to become members of the group is not a vehicular micro cloud in some embodiments.

In some embodiments, a hub of a vehicular micro cloud (and/or a dominant hub of a plurality of vehicular micro clouds) is pre-designated by a vehicle manufacturer by the inclusion of one a bit or a token in a memory of the vehicle at the time of manufacture that designates the vehicle as the hub of all vehicular micro clouds which it joins. Accordingly, if a group of vehicles does not include a hub vehicle having a bit or a token in their memory from the time of manufacture that designates it as the hub for all groups of vehicles that it joins, then this group is not a vehicular micro cloud in some embodiments.

A vehicular micro cloud is not a V2X network or a V2V network. For example, neither a V2X network nor a V2V network include a cluster of vehicles in a same geographic region that are computationally joined to one another as members of a logically associated cluster that make available their unused computing resources to the other members of the cluster. In some embodiments, any of the steps of a method described herein (e.g., the method 300 depicted in FIG. 3) is executed by one or more vehicles which are working together collaboratively using V2X communications for the purpose of completing one or more steps of the method(s). By comparison, solutions which only include V2X networks or V2V networks do not necessarily include the ability of two or more vehicles to work together collaboratively to complete one or more steps of a method.

In some embodiments, a vehicular micro cloud includes vehicles that are parked, vehicles that are traveling in different directions, infrastructure devices, or almost any endpoint that is within communication range of a member of the vehicular micro cloud. By comparison, a group of vehicles that exclude such endpoints as a requirement of being a member of the group are not vehicular micro clouds according to some embodiments.

In some embodiments, a vehicular micro cloud is operable to complete computational tasks itself, without delegation of these computational tasks to a cloud server, using the onboard vehicle computers of its members; this is an example of a vehicular micro cloud task according to some embodiments. In some embodiments, a group of vehicles which relies on a cloud server for its computational analysis, or the difficult parts of its computational analysis, is not a vehicular micro cloud. Although FIG. 1 depicts a server in an operating environment that includes the medic system, the server is an optional feature of the operating environment. An example of a preferred embodiment of the medic system does not include the server in the operating environment which includes the medic system.

In some embodiments, the medic system enables a group of vehicles to perform computationally expensive tasks that could not be completed by any one vehicle in isolation.

An existing solution to vehicular micro cloud task execution involves vehicle platoons. As explained herein, a platoon is not a vehicular micro cloud and does not provide the benefits of a vehicular micro cloud, and some embodiments of the medic system requires vehicular micro cloud; this distinction alone differentiates the medic system from the existing solutions. The medic system is different from the existing solution for additional reasons. For example, the existing solution that relies on vehicle platooning does not include functionality whereby the members of a platoon are changed among the platoons dynamically during the task execution. As another example, the existing solution does not consider the task properties, road geometry, actual and/or predicted traffic information and resource capabilities of vehicles to determine the number of platoons. The existing solution also does not include functionality whereby platoons swap which task or sub-task they are performing among themselves while the tasks or sub-tasks are still being performed by the platoons in parallel. The existing solution also does not include functionality whereby platoons are re-organized based on monitored task executions results/performance and/or available vehicles and resources. As described herein, the medic system includes code and routines that provide, among other things, all of this functionality which is lacking in the existing solution.

Vehicle Control System

Modern vehicles include Advanced Driver Assistance Systems (ADAS systems) or automated driving systems. These systems are referred to herein collectively or individually as "vehicle control systems." An automated driving system includes a sufficient number of ADAS systems so that the vehicle which includes these ADAS systems is rendered autonomous by the benefit of the functionality received by the operation of the ADAS systems by a processor of the vehicle. An example of a vehicle control system according to some embodiments includes the vehicle control system 153 depicted in FIGS. 1 and 2.

A particular vehicle that includes these vehicle control systems is referred to herein as an "ego vehicle" and other vehicles in the vicinity of the ego vehicle as "remote vehicles." As used herein, the term "vehicle" includes a connected vehicle that includes a communication unit and is operable to send and receive V2X communications via a wireless network (e.g., the network 105 depicted in FIG. 1).

Modern vehicles collect a lot of data describing their environment, in particular image data. An ego vehicle uses this image data to understand their environment and operate their vehicle control systems (e.g., ADAS systems or automated driving systems).

As automated vehicles and ADAS systems become increasingly popular, it is important that vehicles have access to the best possible digital data that describes their surrounding environment. In other words, it is important for modern vehicles to have the best possible environmental perception abilities.

Vehicles perceive their surrounding environment by having their onboard sensors record sensor measurements and then analyzing the sensor data to identify one or more of the following: which objects are in their environment; where these objects are located in their environment; and various measurements about these objects (e.g., speed, heading, path history, etc.). This invention is about helping vehicles to have the best possible environmental perception abilities.

Vehicles use their onboard sensors and computing resources to execute perception algorithms that inform them about the objects that are in their environment, where these objects are located in their environment, and various measurements about these objects (e.g., speed, heading, path history, etc.).

Cellular Vehicle to Everything (C-V2X)

C-V2X is an optional feature of the embodiments described herein. Some of the embodiments described herein utilize C-V2X communications. Some of the embodiments described herein do not utilize C-V2X communications. For example, the embodiments described herein utilize V2X communications other than C-V2X communications. C-V2X is defined as 3GPP direct communication (PC5) technologies that include LTE-V2X, 5G NR-V2X, and future 3GPP direct communication technologies.

Dedicated Short-Range Communication (DSRC) is now introduced. A DSRC-equipped device is any processor-based computing device that includes a DSRC transmitter and a DSRC receiver. For example, if a vehicle includes a DSRC transmitter and a DSRC receiver, then the vehicle may be described as "DSRC-enabled" or "DSRC-equipped." Other types of devices may be DSRC-enabled. For example, one or more of the following devices may be DSRC-equipped: an edge server; a cloud server; a roadside unit ("RSU"); a traffic signal; a traffic light; a vehicle; a smartphone; a smartwatch; a laptop; a tablet computer; a personal computer; and a wearable device.

In some embodiments, instances of the term "DSRC" as used herein may be replaced by the term "C-V2X." For example, the term "DSRC radio" is replaced by the term "C-V2X radio," the term "DSRC message" is replaced by the term "C-V2X message," and so on.

In some embodiments, instances of the term "V2X" as used herein may be replaced by the term "C-V2X."

In some embodiments, one or more of the connected vehicles described above are DSRC-equipped vehicles. A DSRC-equipped vehicle is a vehicle that includes a standard-compliant GPS unit and a DSRC radio which is operable to lawfully send and receive DSRC messages in a jurisdiction where the DSRC-equipped vehicle is located. A DSRC radio is hardware that includes a DSRC receiver and a DSRC transmitter. The DSRC radio is operable to wirelessly send and receive DSRC messages on a band that is reserved for DSRC messages.

A DSRC message is a wireless message that is specially configured to be sent and received by highly mobile devices such as vehicles, and is compliant with one or more of the following DSRC standards, including any derivative or fork thereof: EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); and EN 13372:2004 Dedicated Short-Range Communication (DSRC)—DSRC profiles for RTTT applications (review); EN ISO 14906:2004 Electronic Fee Collection—Application interface.

A DSRC message is not any of the following: a WiFi message; a 3G message; a 4G message; an LTE message; a millimeter wave communication message; a Bluetooth message; a satellite communication; and a short-range radio message transmitted or broadcast by a key fob at 315 MHz or 433.92 MHz. For example, in the United States, key fobs for remote keyless systems include a short-range radio transmitter which operates at 315 MHz, and transmissions or broadcasts from this short-range radio transmitter are not DSRC messages since, for example, such transmissions or broadcasts do not comply with any DSRC standard, are not transmitted by a DSRC transmitter of a DSRC radio and are not transmitted at 5.9 GHz. In another example, in Europe and Asia, key fobs for remote keyless systems include a short-range radio transmitter which operates at 433.92 MHz, and transmissions or broadcasts from this short-range radio transmitter are not DSRC messages for similar reasons as those described above for remote keyless systems in the United States.

In some embodiments, a DSRC-equipped device (e.g., a DSRC-equipped vehicle) does not include a conventional global positioning system unit ("GPS unit"), and instead includes a standard-compliant GPS unit. A conventional GPS unit provides positional information that describes a position of the conventional GPS unit with an accuracy of plus or minus 10 meters of the actual position of the conventional GPS unit. By comparison, a standard-compliant GPS unit provides GPS data that describes a position of the standard-compliant GPS unit with an accuracy of plus or minus 1.5 meters of the actual position of the standard-compliant GPS unit. This degree of accuracy is referred to as "lane-level accuracy" since, for example, a lane of a roadway is generally about 3 meters wide, and an accuracy of plus or minus 1.5 meters is sufficient to identify which lane a vehicle is traveling in even when the roadway has more than one lanes of travel each heading in a same direction.

In some embodiments, a standard-compliant GPS unit is operable to identify, monitor and track its two-dimensional position within 1.5 meters, in all directions, of its actual position 68% of the time under an open sky.

GPS data includes digital data describing the location information outputted by the GPS unit.

In some embodiments, the connected vehicle described herein, and depicted in FIG. 1, includes a V2X radio instead of a DSRC radio. In these embodiments, all instances of the term DSRC" as used in this description may be replaced by the term "V2X." For example, the term "DSRC radio" is replaced by the term "V2X radio," the term "DSRC message" is replaced by the term "V2X message," and so on.

75 MHz of the 5.9 GHz band may be designated for DSRC. However, in some embodiments, the lower 45 MHz of the 5.9 GHz band (specifically, 5.85-5.895 GHz) is reserved by a jurisdiction (e.g., the United States) for unlicensed use (i.e., non-DSRC and non-vehicular related use) whereas the upper 30 MHz of the 5.9 GHz band (specifically, 5.895-5.925 GHz) is reserved by the jurisdiction for Cellular Vehicle to Everything (C-V2X) use. In these embodiments, the V2X radio depicted in FIG. 1 is a C-V2X radio which is operable to send and receive C-V2X wireless messages on the upper 30 MHz of the 5.9 GHz band (i.e., 5.895-5.925 GHz). In these embodiments, the medic system 199 is operable to cooperate with the C-V2X radio and provide its functionality using the content of the C-V2X wireless messages.

In some of these embodiments, some or all of the digital data depicted in FIG. 1 is the payload for one or more C-V2X messages. In some embodiments, the C-V2X message is a BSM.

Vehicular Network

In some embodiments, the medic system utilizes a vehicular network. A vehicular network includes, for example, one or more of the following: V2V; V2X; vehicle-to-network-to-vehicle (V2N2V); vehicle-to-infrastructure (V2I); C-V2X; any derivative or combination of the networks listed herein; and etc.

In some embodiments, the medic system includes software installed in an onboard unit of a connected vehicle. This software is the "medic system" described herein.

An example operating environment for the embodiments described herein includes an ego vehicle, one or more remote vehicles, and a recipient vehicle. The ego vehicle the remote connected vehicle are connected vehicles having communication units that enable them to send and receive wireless messages via one or more vehicular networks. In some embodiments, the recipient vehicle is a connected vehicle. In some embodiments, the ego vehicle and the remote connected vehicle include an onboard unit having a medic system stored therein.

Some of the embodiments described herein include a server. However, some of the embodiments described herein do not include a server. A serverless operating environment is an operating environment which includes at least one medic system and does not include a server.

Figure 3:
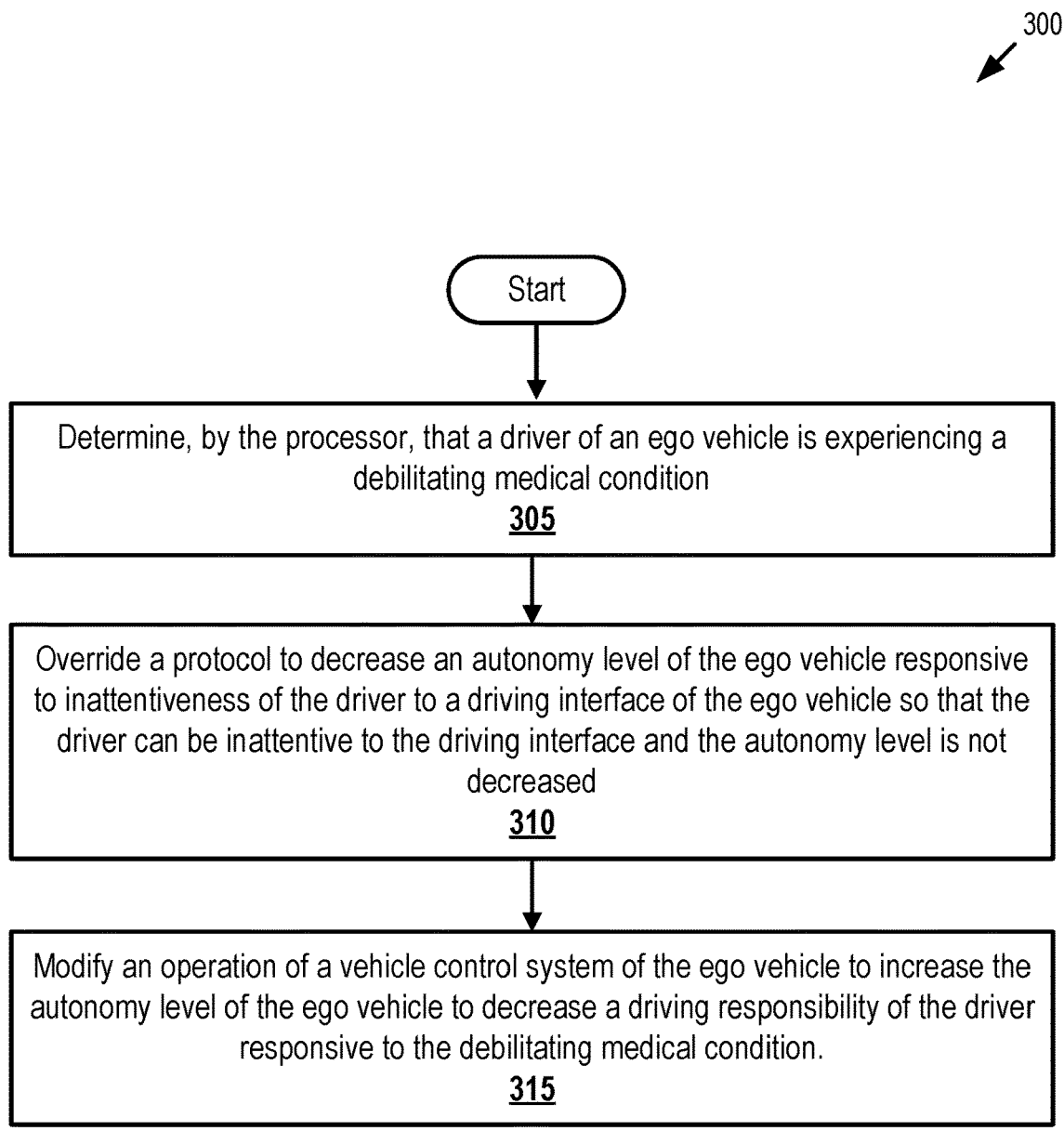
FIG. 3 is a flowchart of an example method for providing a medic service according to some embodiments.
Figure 4A:
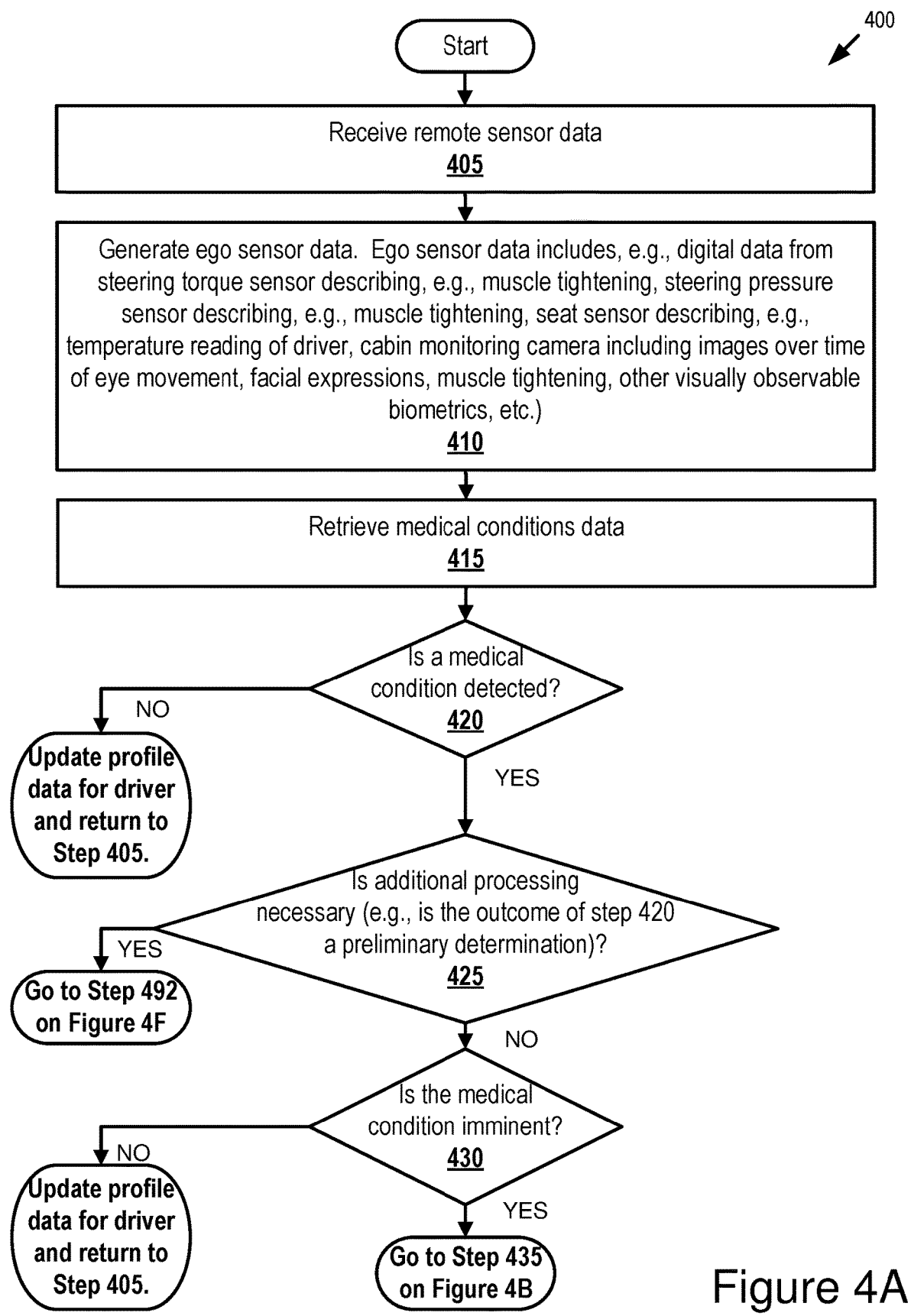
FIGS. 4A-4F is a flowchart of an example method for providing a medic service according to some embodiments.
Figure 4B:
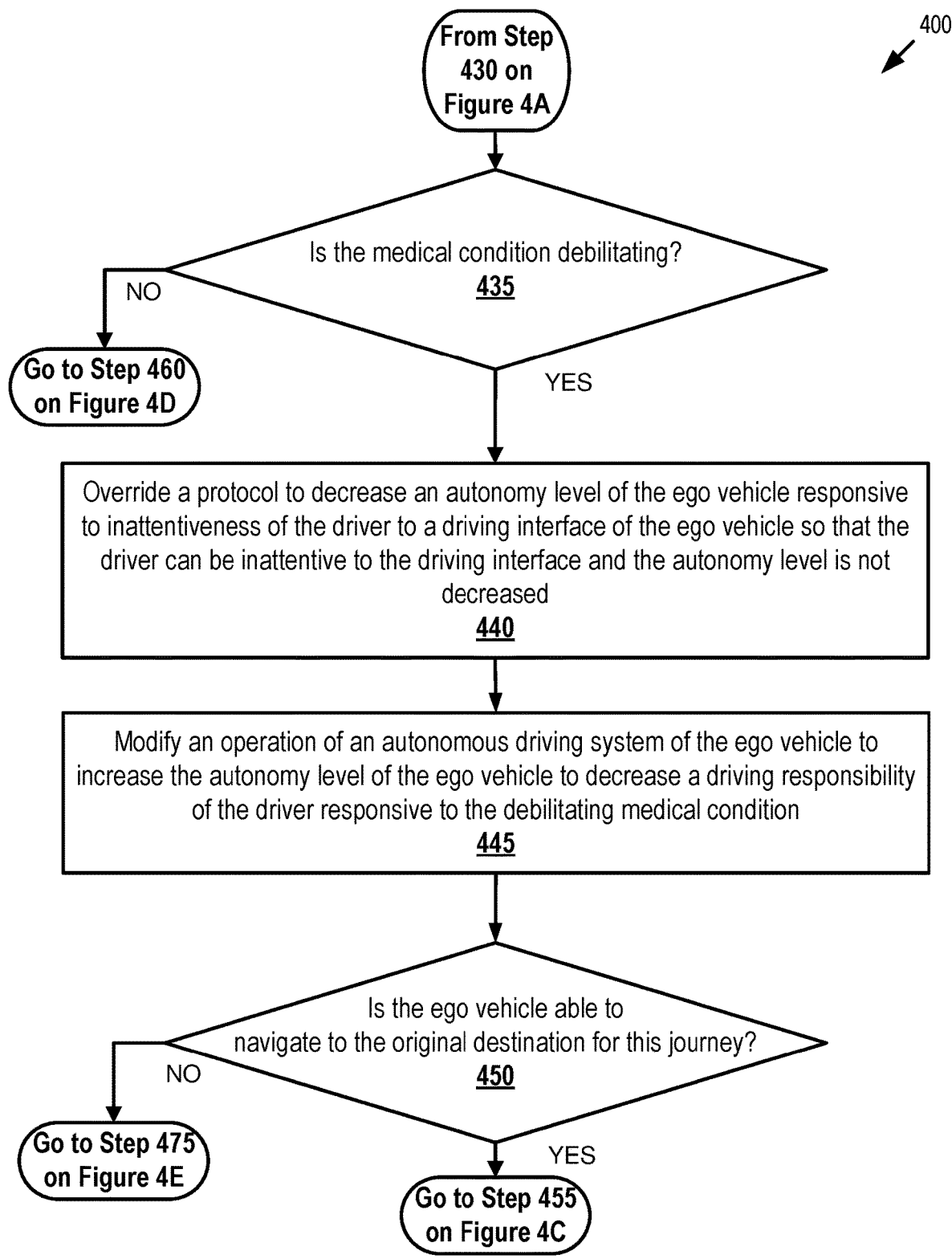
Figure 4C:
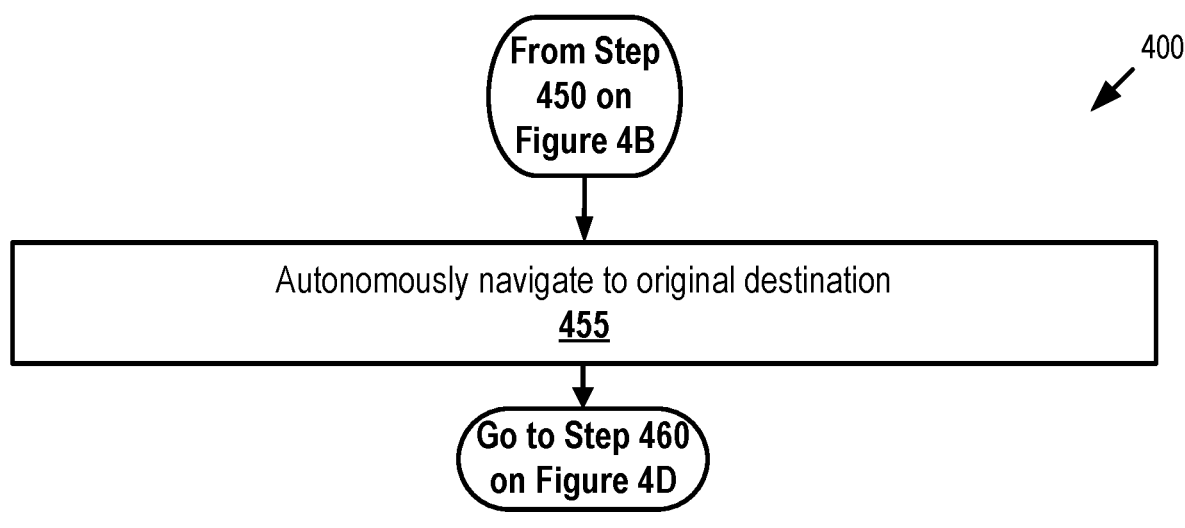
Figure 4D:
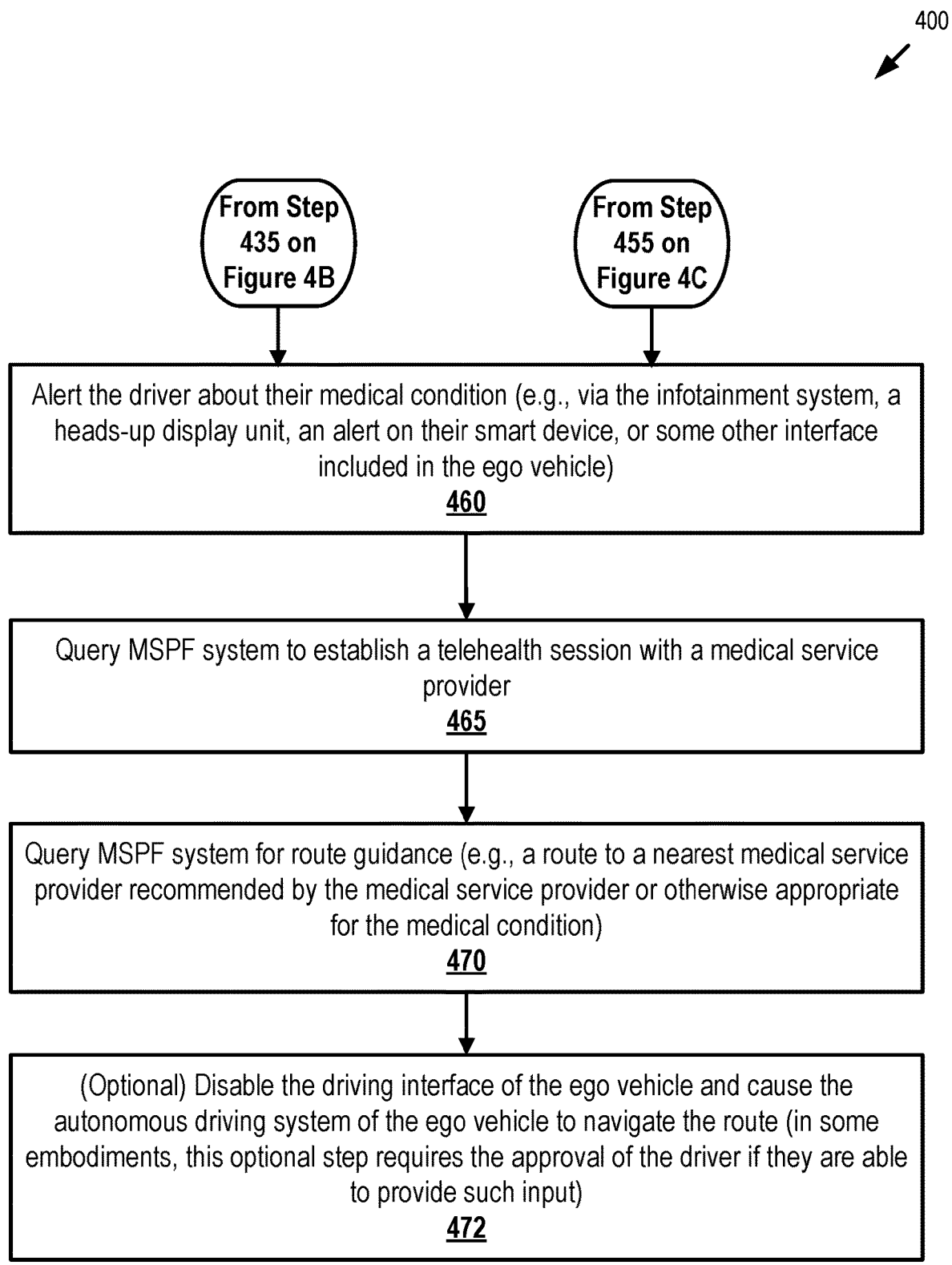
Figure 4E:
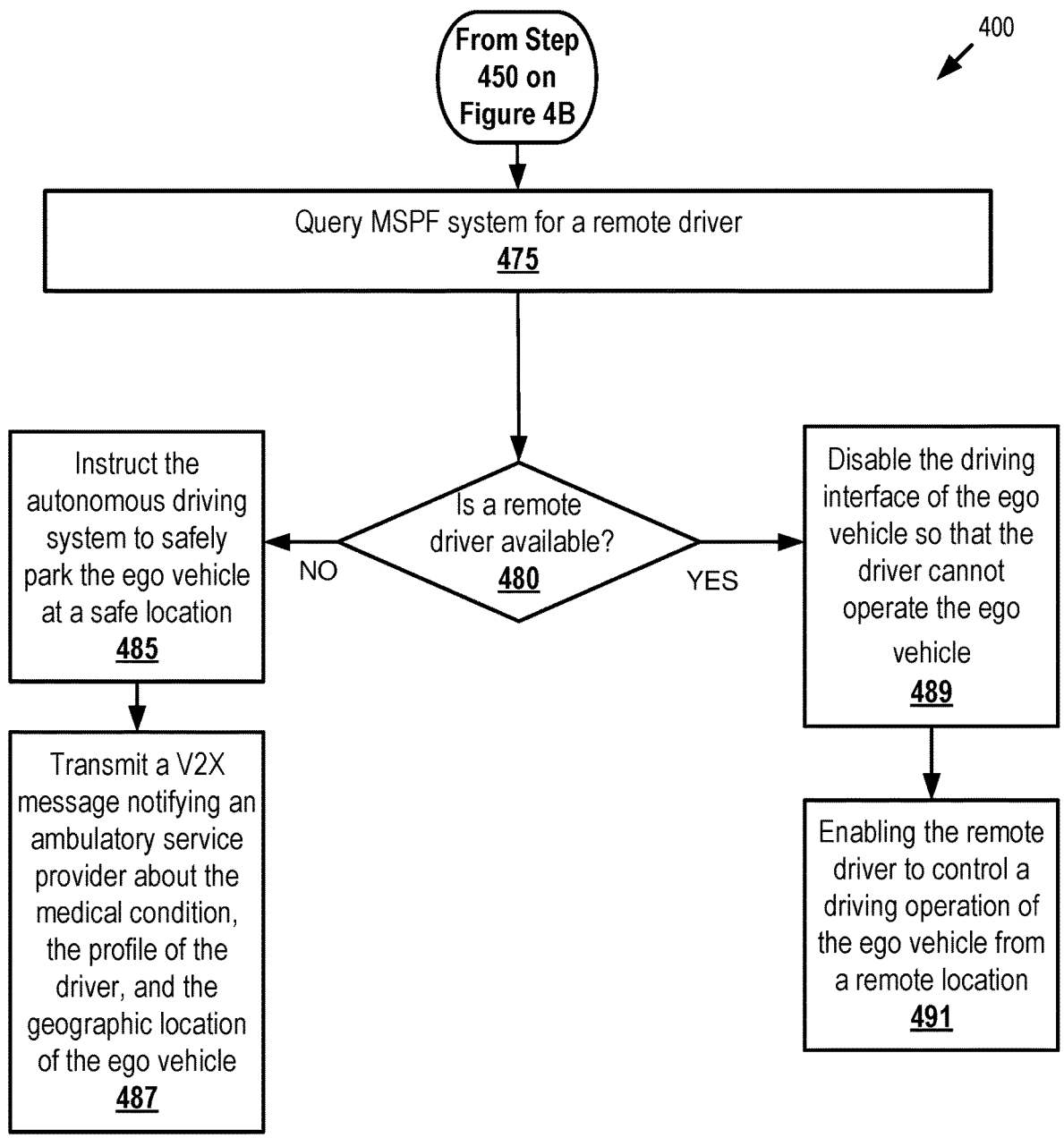
Figure 4F:
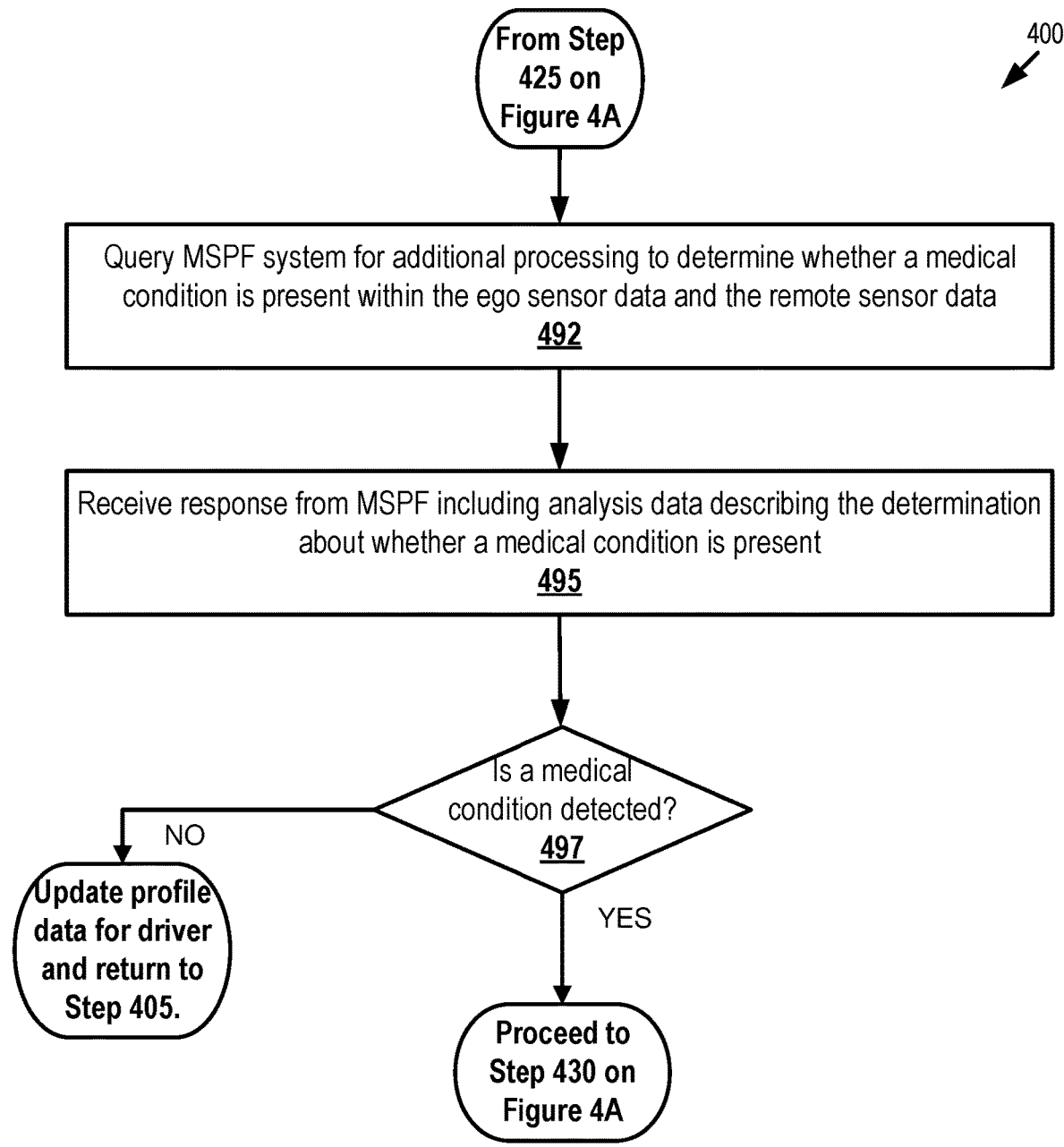

In some embodiments, the medic system includes code and routines that are operable, when executed by a processor of the onboard unit, to cause the processor to execute one or more of the steps of the method 300 depicted in FIG. 3, the method 400 depicted in FIGS. 4A, 4B, 4C, 4D, 4E, and 4F, or any other method described herein (e.g., the example general method).

This patent application is related to U.S. patent application Ser. No. 15/644,197 filed on Jul. 7, 2017 and entitled "Computation Service for Mobile Nodes in a Roadway Environment," the entirety of which is hereby incorporated by reference. This patent application is also related to U.S. patent application Ser. No. 16/457,612 filed on Jun. 28, 2019 and entitled "Context System for Providing Cyber Security for Connected Vehicles," the entirety of which is hereby incorporated by reference.

Example Overview

In some embodiments, the medic system is software that is operable, when executed by a processor, to cause the processor to execute one or more of the methods described herein. An example operating environment 100 for the medic system is depicted in FIG. 1.

In some embodiments, the medic system 199 is software installed in an onboard unit (e.g., an electronic control unit (ECU)) of a particular make of vehicle having V2X communication capability. For example, the ego vehicle 123 includes a communication unit 145. The communication unit 145 includes a V2X radio. For example, the communication unit 145 includes a C-V2X radio. FIG. 1 depicts an example operating environment 100 for the medic system 199 according to some embodiments.

In some embodiments, the remote vehicle 124 is a connected vehicle, which is a vehicle such as the remote vehicle 124 or the ego vehicle 123 having V2X communication capability. In some embodiments, the remote vehicle 124 is not a connected vehicle. The ego vehicle 123 is a connected vehicle. In some embodiments, the remote vehicle 124 is an ambulatory service provider. An example of an ambulatory service provider includes an ambulance, a helicopter that delivers people to a medicals service provider, or some other mobile medical service provider.

Example Operative Environment

Embodiments of the medic system are now described. Referring now to FIG. 1, depicted is a block diagram illustrating an operating environment 100 for a medic system 199 according to some embodiments. The operating environment 100 is present in a roadway environment 140. In some embodiments, each of the elements of the operating environment 100 is present in the same roadway environment 140 at the same time. In some embodiments, some of the elements of the operating environment 100 are not present in the same roadway environment 140 at the same time.

The roadway environment 140 includes objects. Examples of objects include one or of the following: other automobiles, road surfaces; signs, traffic signals, roadway paint, medians, turns, intersections, animals, pedestrians, debris, potholes, accumulated water, accumulated mud, gravel, roadway construction, cones, bus stops, poles, entrance ramps, exit ramps, breakdown lanes, merging lanes, other lanes, railroad tracks, railroad crossings, and any other tangible object that is present in a roadway environment 140 or otherwise observable or measurable by a camera or some other sensor included in the sensor set.

The operating environment 100 may include one or more of the following elements: an ego vehicle 123 (referred to herein as a "vehicle 123" or an "ego vehicle 123") (which has a driver 109 in embodiments where the ego vehicle 123 is not at least a Level 3 autonomous vehicle); a remote vehicle 124 (which has a driver similar to the driver 109 in embodiments where the remote vehicle 124 is not at least a Level 3 autonomous vehicle); a cloud server 103; and an edge server 198. These elements are communicatively coupled to one another via a network 105. These elements of the operating environment 100 are depicted by way of illustration. In practice, the operating environment 100 may include one or more of the elements depicted in FIG. 1. For example, although only two vehicles 123, 124 are depicted in FIG. 1, in practice the operating environment 100 can include a plurality of these elements.

In some embodiments, one or more of the ego vehicle 123, the remote vehicle 124, the edge server 198, and the network 105 are elements (e.g., members) of a vehicular micro cloud 194. The operating environment 100 includes a plurality of vehicular micro clouds 194 as depicted in FIG. 1. In some embodiments, the operating environment 100 also includes a plurality of remote vehicles 124. These remote vehicles 124 may be different from one another. For example, a first remote vehicle 124 is an ambulance whereas a plurality of second remote vehicles 124 are not ambulances.

In some embodiments, the ego vehicle 123 and the one or more remote vehicle 124 are member of one or more of the plurality of vehicular micro clouds 194; the memberships of the ego vehicle 123 and the one or more remote vehicles in the plurality of vehicular micro clouds 194 may or may not be similar.

In some embodiments, the ego vehicle 123 and the remote vehicle 124 include similar elements. For example, each of these elements of the operating environment 100 include their own processor 125, bus 121, memory 127, communication unit 145, processor 125, sensor set 126, onboard unit 139, cabin sensors 150 and medic system 199. These elements of the ego vehicle 123 and the remote vehicle 124 provide the same or similar functionality regardless of whether they are included in the ego vehicle 123 or the remote vehicle 124. Accordingly, the descriptions of these elements will not be repeated in this description for each of the ego vehicle 123 and the remote vehicle 124.

In the depicted embodiment, the ego vehicle 123 and the remote vehicle 124 store similar digital data. The system data 129 includes digital data that describes some or all of the digital data stored in the memory 127 or otherwise described herein. The system data 129 is depicted in FIG. 1 as being an element of the cloud server 103, but in practice the system data 129 is stored on one or more of the cloud server 103, the edge server 198, the ego vehicle 123, and one or more of the remote vehicles 124.

In some embodiments, the one or more of the vehicular micro clouds 194 are a stationary vehicular micro cloud such as described by U.S. patent application Ser. No. 15/799,964 filed on Oct. 31, 2017 and entitled "Identifying a Geographic Location for a Stationary Micro-Vehicular Cloud," the entirety of which is herein incorporated by reference. In some embodiments, one or more of the vehicular micro clouds 194 is a mobile vehicular micro cloud. For example, each of the ego vehicle 123 and the remote vehicle 124 are vehicular micro cloud members because they are connected endpoints that are members of the vehicular micro cloud 194 that can access and use the unused computing resources (e.g., their unused processing power, unused data storage, unused sensor capabilities, unused bandwidth, etc.) of the other vehicular micro cloud members using wireless communications that are transmitted via the network 105 and these wireless communicates are not required to be relayed through a cloud server. As used herein, the terms a "vehicular micro cloud" and a "micro-vehicular cloud" mean the same thing.

In some embodiments, the vehicular micro cloud 194 is a vehicular micro cloud such as the one described in U.S. patent application Ser. No. 15/799,963 filed on Oct. 31, 2017 and entitled "Identifying a Geographic Location for a Stationary Micro-Vehicular Cloud."

In some embodiments, the vehicular micro cloud 194 includes a dynamic vehicular micro cloud. In some embodiments, the vehicular micro cloud 194 includes an interdependent vehicular micro cloud. In some embodiments, the vehicular micro cloud 194 is sub-divided into a set of nano clouds.

As described above, in some embodiments operating environment 100 includes a plurality of vehicular micro clouds 194. For example, the operating environment 100 includes a first vehicular micro cloud and a second vehicular micro cloud. The operating environment 100 can include any positive whole number of vehicular micro clouds 194 that is greater than one.

Vehicular micro clouds are an optional component of the operating environment 100. In some embodiments, the operating environment 100 does not include a vehicular micro cloud 194. The medic system 199 does not require a vehicular micro cloud 194 to provide its functionality.

In some embodiments, a vehicular micro cloud 194 is not a V2X network or a V2V network because, for example, such networks do not include allowing endpoints of such networks to access and use the unused computing resources of the other endpoints of such networks. By comparison, a vehicular micro cloud 194 requires allowing all members of the vehicular micro cloud 194 to access and use designated unused computing resources of the other members of the vehicular micro cloud 194. In some embodiments, endpoints must satisfy a threshold of unused computing resources in order to join the vehicular micro cloud 194. The hub vehicle of the vehicular micro cloud 194 executes a process to: (1) determine whether endpoints satisfy the threshold as a condition for joining the vehicular micro cloud 194; and (2) determine whether the endpoints that do join the vehicular micro cloud 194 continue to satisfy the threshold after they join as a condition for continuing to be members of the vehicular micro cloud 194.

In some embodiments, a member of the vehicular micro cloud 194 includes any endpoint (e.g., the ego vehicle 123, the remote vehicle 124, the edge server 198, etc.) which has completed a process to join the vehicular micro cloud 194

(e.g., a handshake process with the coordinator of the vehicular micro cloud 194). The cloud server 103 is excluded from membership in the vehicular micro cloud 194 in some embodiments. A member of the vehicular micro cloud 194 is described herein as a "member" or a "micro cloud member." In some embodiments, a coordinator of the vehicular micro cloud 194 is the hub of the vehicular micro cloud (e.g., the ego vehicle 123).

In some embodiments, the memory 127 of one or more of the endpoints stores member data 171. The member data 171 is digital data that describes one or more of the following: the identity of each of the micro cloud members; what digital data, or bits of data, are stored by each micro cloud member; what computing services are available from each micro cloud member; what computing resources are available from each micro cloud member and what quantity of these resources are available; and how to communicate with each micro cloud member.

In some embodiments, the member data 171 describes logical associations between endpoints which are a necessary component of the vehicular micro cloud 194 and serves to differentiate the vehicular micro cloud 194 from a mere V2X network. In some embodiments, a vehicular micro cloud 194 must include a hub vehicle and this is a further differentiation from a vehicular micro cloud 194 and a V2X network or a group, clique, or platoon of vehicles which is not a vehicular micro cloud 194.

In some embodiments, the member data 171 describes the logical associations between more than one vehicular micro cloud. For example, the member data 171 describes the logical associations between the first vehicular micro cloud and the second vehicular micro cloud. Accordingly, in some embodiments the memory 127 includes member data 171 for more than one vehicular micro cloud 194.

The member data 171 also describes the digital data described above with reference to a dominant hub and the example general method.

In some embodiments, the vehicular micro cloud 194 does not include a hardware server. Accordingly, in some embodiments the vehicular micro cloud 194 may be described as serverless.

In some embodiments, the vehicular micro cloud 194 includes a hardware server. For example, in some embodiments the vehicular micro cloud 194 includes the cloud server 103.

The network 105 is a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices and/or entities may communicate. In some embodiments, the network 105 may include a peer-to-peer network. The network 105 may also be coupled to or may include portions of a telecommunications network for sending data in a variety of different communication protocols. In some embodiments, the network 105 includes Bluetooth® communication networks or a cellular communications network for sending and receiving data including via short messaging service (SMS), multimedia messaging service (MMS), hypertext transfer protocol (HTTP), direct data connection, wireless application protocol (WAP), e-mail, DSRC, full-duplex wireless communication, mmWave, WiFi (infrastructure mode), WiFi (ad-hoc mode), visible light communication, TV white space communication and satellite communication. The network 105 may also include a mobile data network that may include 3G, 4G, 5G, millimeter wave (mmWave), LTE, LTE-V2X, LTE-D2D, VoLTE or any other mobile data network or combination of mobile data networks. Further, the network 105 may include one or more IEEE 802.11 wireless networks.

In some embodiments, the network 105 is a V2X network. For example, the network 105 must include a vehicle, such as the ego vehicle 123, as an originating endpoint for each wireless communication transmitted by the network 105. An originating endpoint is the endpoint that initiated a wireless communication using the network 105. In some embodiments, the network 105 is a vehicular network. In some embodiments, the network 105 is a C-V2X network.

In some embodiments, the network 105 is an element of the vehicular micro cloud 194. Accordingly, the vehicular micro cloud 194 is not the same thing as the network 105 since the network is merely a component of the vehicular micro cloud 194. For example, the network 105 does not include member data. The network 105 also does not include a hub vehicle.

In some embodiments, one or more of the ego vehicle 123 and the remote vehicle 124 are C-V2X equipped vehicles. For example, the ego vehicle 123 includes a standard-compliant GPS unit that is an element of the sensor set 126 and a C-V2X radio that is an element of the communication unit 145. The network 105 may include a C-V2X communication channel shared among the ego vehicle 123 and a second vehicle such as the remote vehicle 124.

A C-V2X radio is hardware radio that includes a C-V2X receiver and a C-V2X transmitter. The C-V2X radio is operable to wirelessly send and receive C-V2X messages on a band that is reserved for C-V2X messages.

The ego vehicle 123 includes a car, a truck, a sports utility vehicle, a bus, a semi-truck, a drone, or any other roadway-based conveyance. In some embodiments, the ego vehicle 123 includes an autonomous vehicle or a semi-autonomous vehicle. Although not depicted in FIG. 1, in some embodiments, the ego vehicle 123 includes an autonomous driving system. The autonomous driving system includes code and routines that provides sufficient autonomous driving features to the ego vehicle 123 to render the ego vehicle 123 an autonomous vehicle or a highly autonomous vehicle. In some embodiments, the ego vehicle 123 is a Level III autonomous vehicle or higher as defined by the National Highway Traffic Safety Administration and the Society of Automotive Engineers. In some embodiments, the vehicle control system 153 is an autonomous driving system.

The ego vehicle 123 is a connected vehicle. For example, the ego vehicle 123 is communicatively coupled to the network 105 and operable to send and receive messages via the network 105. For example, the ego vehicle 123 transmits and receives V2X messages via the network 105.

In some embodiments, the ego vehicle 123 is operable to be placed in "drone mode" which enables the ego vehicle 123 to be operated by the remote system 149. When in drone mode the driving interface of the ego vehicle 123 is disengaged so that any input to the driving interface is not operable to control the operation of the ego vehicle 123. Instead, the operation of the ego vehicle 123 is controlled remotely by the remote system 149 which is itself operated by one or more of a human, software, and a combination of a human and software. In this way, the ego vehicle 123 is operable to be driven by a remote source, i.e., the remote system 149.

For example, the remote system 149 provides wireless messages that include commands that are operable to control the operation of the ego vehicle 123 via the network 105.

The communication unit 145 receives the wireless messages via the network 105. The medic system 199 of the ego vehicle 123 parses out the commands from the wireless messages and transmits them to the vehicle control system 153 of the ego vehicle 123. The vehicle control system 153 then controls the operation of the ego vehicle 123 consistent with these commands. This process is repeated as more wireless messages are received from the remote system 149 via the network 105.

The ego vehicle 123 includes one or more of the following elements: a processor 125; a sensor set 126; cabin sensors 150; a vehicle control system 153; a communication unit 145; an onboard unit 139; a memory 127; and a medic system 199. These elements may be communicatively coupled to one another via a bus 121. In some embodiments, the communication unit 145 includes a V2X radio.

The processor 125 includes an arithmetic logic unit, a microprocessor, a general-purpose controller, or some other processor array to perform computations and provide electronic display signals to a display device. The processor 125 processes data signals and may include various computing architectures including a complex instruction set computer (CISC) architecture, a reduced instruction set computer (RISC) architecture, or an architecture implementing a combination of instruction sets. Although FIG. 1 depicts a single processor 125 present in the ego vehicle 123, multiple processors may be included in the ego vehicle 123. The processor 125 may include a graphical processing unit. Other processors, operating systems, sensors, displays, and physical configurations may be possible.

In some embodiments, the processor 125 is an element of a processor-based computing device of the ego vehicle 123. For example, the ego vehicle 123 may include one or more of the following processor-based computing devices and the processor 125 may be an element of one of these devices: an onboard vehicle computer; an electronic control unit; a navigation system; a vehicle control system (e.g., an ADAS system or autonomous driving system); and a head unit. In some embodiments, the processor 125 is an element of the onboard unit 139.

The onboard unit 139 is a special purpose processor-based computing device. In some embodiments, the onboard unit 139 is a communication device that includes one or more of the following elements: the communication unit 145; the processor 125; the memory 127; and the medic system 199. In some embodiments, the onboard unit 139 is the computer system 200 depicted in FIG. 2. In some embodiments, the onboard unit 139 is an electronic control unit (ECU).

The sensor set 126 includes one or more onboard sensors. The sensor set 126 records sensor measurements that describe the ego vehicle 123 and/or the physical environment (e.g., the roadway environment 140) that includes the ego vehicle 123. The ego sensor data 195 includes digital data that describes the sensor measurements.

In some embodiments, the sensor set 126 may include one or more sensors that are operable to measure the physical environment outside of the ego vehicle 123. For example, the sensor set 126 may include cameras, lidar, radar, sonar and other sensors that record one or more physical characteristics of the physical environment that is proximate to the ego vehicle 123.

In some embodiments, the sensor set 126 may include one or more sensors that are operable to measure the physical environment inside a cabin of the ego vehicle 123. For example, the sensor set 126 may record an eye gaze of the driver (e.g., using an internal camera), where the driver's hands are located (e.g., using an internal camera) and whether the driver is touching a head unit or infotainment system with their hands (e.g., using a feedback loop from the head unit or infotainment system that indicates whether the buttons, knobs or screen of these devices is being engaged by the driver).

In some embodiments, the sensor set 126 may include one or more of the following sensors: an altimeter; a gyroscope; a proximity sensor; a microphone; a microphone array; an accelerometer; a camera (internal or external); a LIDAR sensor; a laser altimeter; a navigation sensor (e.g., a global positioning system sensor of the standard-compliant GPS unit); an infrared detector; a motion detector; a thermostat; a sound detector, a carbon monoxide sensor; a carbon dioxide sensor; an oxygen sensor; a mass air flow sensor; an engine coolant temperature sensor; a throttle position sensor; a crank shaft position sensor; an automobile engine sensor; a valve timer; an air-fuel ratio meter; a blind spot meter; a curb feeler; a defect detector; a Hall effect sensor, a manifold absolute pressure sensor; a parking sensor; a radar gun; a speedometer; a speed sensor; a tire-pressure monitoring sensor; a torque sensor; a transmission fluid temperature sensor; a turbine speed sensor (TSS); a variable reluctance sensor; a vehicle speed sensor (VSS); a water sensor; a wheel speed sensor; and any other type of automotive sensor.

The sensor set 126 is operable to record ego sensor data 195. The ego sensor data 195 includes digital data that describes images or other measurements of the physical environment such as the conditions, objects, and other vehicles present in the roadway environment. Examples of objects include pedestrians, animals, traffic signs, traffic lights, potholes, etc. Examples of conditions include weather conditions, road surface conditions, shadows, leaf cover on the road surface, any other condition that is measurable by a sensor included in the sensor set 126.

The physical environment may include a roadway region, parking lot, or parking garage that is proximate to the ego vehicle 123. In some embodiments, the roadway environment 140 includes a roadway that includes a roadway region. The ego sensor data 195 may describe measurable aspects of the physical environment. In some embodiments, the physical environment is the roadway environment 140. As such, in some embodiments, the roadway environment 140 includes one or more of the following: a roadway region that is proximate to the ego vehicle 123; a parking lot that is proximate to the ego vehicle 123; a parking garage that is proximate to the ego vehicle 123; the conditions present in the physical environment proximate to the ego vehicle 123; the objects present in the physical environment proximate to the ego vehicle 123; and other vehicles present in the physical environment proximate to the ego vehicle 123; any other tangible object that is present in the real-world and proximate to the ego vehicle 123 or otherwise measurable by the sensors of the sensor set 126 or whose presence is determinable from the digital data stored on the memory 127. An item is "proximate to the ego vehicle 123" if it is directly measurable by a sensor of the ego vehicle 123 or its presence is inferable and/or determinable by the medic system 199 based on analysis of the ego sensor data 195 which is recorded by the ego vehicle 123 and/or one or more members of the vehicular micro cloud 194.

The sensor set 126 also includes the cabin sensors 150. The cabin sensors 150 and the cabin data 155 they generate are described above, and so, these descriptions will not be repeated here.

In some embodiments, the ego sensor data 195 includes digital data that describes all of the sensor measurements recorded by the sensor set 126 of the ego vehicle.

For example, the ego sensor data 195 includes, among other things, one or more of the following: lidar data (i.e., depth information) recorded by an ego vehicle; or camera data (i.e., image information) recorded by the ego vehicle. The lidar data includes digital data that describes depth information about a roadway environment 140 recorded by a lidar sensor of a sensor set 126 included in the ego vehicle 123. The camera data includes digital data that describes the images recorded by a camera of the sensor set 126 included in the ego vehicle 123. The depth information and the images describe the roadway environment 140, including tangible objects in the roadway environment 140 and any other physical aspects of the roadway environment 140 that are measurable using a depth sensor and/or a camera.

In some embodiments, the sensors of the sensor set 126 are operable to collect ego sensor data 195. The sensors of the sensor set 126 include any sensors that are necessary to measure and record the measurements described by the ego sensor data 195. In some embodiments, the ego sensor data 195 includes any sensor measurements that are necessary to generate the other digital data stored by the memory 127. In some embodiments, the ego sensor data 195 includes digital data that describes any sensor measurements that are necessary for the medic system 199 provides its functionality as described herein with reference to the method 300 depicted in FIG. 3, the method 400 depicted in FIGS. 4A-4F, and/or the example general method described herein.

In some embodiments, the sensor set 126 includes any sensors that are necessary to record ego sensor data 195 that describes the roadway environment 140 in sufficient detail to create a digital twin of the roadway environment 140. In some embodiments, the medic system 199 generates the set of nano clouds and assigns sub-tasks to the nano clouds based on the outcomes observed by the medic system 199 during the execution of a set of digital twins that simulate the real-life circumstances of the ego vehicle 123.

In some embodiments the medic system 199 includes simulation software. The simulation software is any simulation software that is capable of simulating an execution of a vehicular micro cloud task. For example, the simulation software is operable simulate the medic system 199 providing its functionality to generate some or all of the system data 129. In some embodiments, the simulation software is operable to determine a remedial action plan for a medical condition, intercept routes for the ego vehicle 123 and a remote vehicle 124 to travel, or the output of any other analysis or process described herein.

A digital twin is a simulated version of a specific real-world vehicle that exists in a simulation. A structure, condition, behavior, and responses of the digital twin are similar to a structure, condition, behavior, and responses of the specific real-world vehicle that the digital twin represents in the simulation. The digital environment included in the simulation is similar to the real-world roadway environment 140 of the real-world vehicle. The simulation software includes code and routines that are operable to execute simulations based on digital twins of real-world vehicles in the roadway environment.

In some embodiments, the simulation software is integrated with the medic system 199. In some other embodiments, the simulation software is a standalone software that the medic system 199 can access to execute digital twin simulations. In some embodiments, the medic system 199 uses the digital twin simulations to determine one or more of the following: analysis data 181; reaction data 173; medical conditions data 174; and routing data 176.

Digital twin data 162 includes any digital data, software, and/or other information that is necessary to execute the digital twin simulations.

Digital twins, and an example process for generating and using digital twins which is implemented by the medic system 199 in some embodiments, are described in U.S. patent application Ser. No. 16/521,574 entitled "Altering a Vehicle based on Driving Pattern Comparison" filed on Jul. 24, 2019, the entirety of which is hereby incorporated by reference.

The ego sensor data 195 includes digital data that describes any measurement that is taken by one or more of the sensors of the sensor set 126.

The standard-compliant GPS unit includes a GPS unit that is compliant with one or more standards that govern the transmission of V2X wireless communications ("V2X communication" if singular, "V2X communications" if plural). For example, some V2X standards require that BSMs are transmitted at intervals by vehicles and that these BSMs must include within their payload GPS data having one or more attributes. In some embodiments, the standard-compliant GPS unit is an element of the sensor set 126.

An example of an attribute for GPS data is accuracy. In some embodiments, the standard-compliant GPS unit is operable to generate GPS measurements which are sufficiently accurate to describe the location of the ego vehicle 123 with lane-level accuracy. Lane-level accuracy is necessary to comply with some of the existing and emerging standards for V2X communication (e.g., C-V2X communication). Lane-level accuracy means that the GPS measurements are sufficiently accurate to describe which lane of a roadway that the ego vehicle 123 is traveling (e.g., the geographic position described by the GPS measurement is accurate to within 1.5 meters of the actual position of the ego vehicle 123 in the real-world). Lane-level accuracy is described in more detail below.

In some embodiments, the standard-compliant GPS unit is compliant with one or more standards governing V2X communications but does not provide GPS measurements that are lane-level accurate.

In some embodiments, the standard-compliant GPS unit includes any hardware and software necessary to make the ego vehicle 123 or the standard-compliant GPS unit compliant with one or more of the following standards governing V2X communications, including any derivative or fork thereof: EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); and EN 13372:2004 Dedicated Short-Range Communication (DSRC)—DSRC profiles for RTTT applications (review); EN ISO 14906:2004 Electronic Fee Collection—Application interface.

In some embodiments, the standard-compliant GPS unit is operable to provide GPS data describing the location of the ego vehicle 123 with lane-level accuracy. For example, the ego vehicle 123 is traveling in a lane of a multi-lane roadway. Lane-level accuracy means that the lane of the ego vehicle 123 is described by the GPS data so accurately that a precise lane of travel of the ego vehicle 123 may be accurately determined based on the GPS data for this ego vehicle 123 as provided by the standard-compliant GPS unit.

An example process for generating GPS data describing a geographic location of an object (e.g., a vehicle, a roadway object, an object of interest, a remote vehicle 124, the ego vehicle 123, or some other tangible object or construct located in a roadway environment 140) is now described according to some embodiments. In some embodiments, the medic system 199 include code and routines that are operable, when executed by the processor 125, to cause the processor to: analyze (1) GPS data describing the geographic location of the ego vehicle 123 and (2) ego sensor data describing the range separating the ego vehicle 123 from an object and a heading for this range; and determine, based on this analysis, GPS data describing the location of the object. The GPS data describing the location of the object may also have lane-level accuracy because, for example, it is generated using accurate GPS data of the ego vehicle 123 and accurate sensor data describing information about the object.

In some embodiments, the standard-compliant GPS unit includes hardware that wirelessly communicates with a GPS satellite (or GPS server) to retrieve GPS data that describes the geographic location of the ego vehicle 123 with a precision that is compliant with a V2X standard. One example of a V2X standard is the DSRC standard. Other standards governing V2X communications are possible. The DSRC standard requires that GPS data be precise enough to infer if two vehicles (one of which is, for example, the ego vehicle 123) are located in adjacent lanes of travel on a roadway. In some embodiments, the standard-compliant GPS unit is operable to identify, monitor and track its two-dimensional position within 1.5 meters of its actual position 68% of the time under an open sky. Since roadway lanes are typically no less than 3 meters wide, whenever the two-dimensional error of the GPS data is less than 1.5 meters the medic system 199 described herein may analyze the GPS data provided by the standard-compliant GPS unit and determine what lane the ego vehicle 123 is traveling in based on the relative positions of two or more different vehicles (one of which is, for example, the ego vehicle 123) traveling on a roadway at the same time.

By comparison to the standard-compliant GPS unit, a conventional GPS unit which is not compliant with the DSRC standard is unable to determine the location of a vehicle (e.g., the ego vehicle 123) with lane-level accuracy. For example, a typical roadway lane is approximately three meters wide. However, a conventional GPS unit only has an accuracy of plus or minus 10 meters relative to the actual location of the ego vehicle 123. As a result, such conventional GPS units are not sufficiently accurate to enable the medic system 199 to determine the lane of travel of the ego vehicle 123. This measurement improves the accuracy of the GPS data describing the location of lanes used by the ego vehicle 123 when the medic system 199 is providing its functionality.

In some embodiments, the standard-compliant GPS unit enables the medic system 199 to calculate more accurate routes as described by the route data 176.

In some embodiments, the memory 127 stores two types of GPS data. The first is GPS data of the ego vehicle 123 and the second is GPS data of one or more objects (e.g., the remote vehicle 124 or some other object in the roadway environment). The GPS data of the ego vehicle 123 is digital data that describes a geographic location of the ego vehicle 123. The GPS data of the objects is digital data that describes a geographic location of an object. One or more of these two types of GPS data may have lane-level accuracy.

In some embodiments, one or more of these two types of GPS data are described by the ego sensor data 195. For example, the standard-compliant GPS unit is a sensor included in the sensor set 126 and the GPS data is an example type of ego sensor data 195.

In some embodiments, the medic system 199 causes an electronic display of the ego vehicle 123 to display a message describing information relating to the functionality provided by the medic system 199. For example, the medic system 199 causes an electronic display of the ego vehicle 123 to display a message describing one or more of the following: a medical condition detected by the medic system 199; a remedial action plan to respond to the medical condition; questions that enable the occupant to provide input to help the medic system diagnose the medical condition or assess whether it is debilitating; questions to acquire the profile data 184; information to enable or facilitate a telehealth visit; etc. The message is displayed as an element of a graphical user interface (GUI). GUI data 187 includes digital data that describes the GUI that includes the message. The medic system 199 generates and outputs the GUI data 187.

In some embodiments, the GUI is displayed on an electronic display (not depicted) of the ego vehicle 123. In some embodiments, the medic system 199 is communicatively coupled to the electronic display to provide the GUI data 187 to the electronic display and control the operation of the electronic display to display the GUI. In some embodiments, the electronic display is a touchscreen that is also operated to receive inputs from the occupant of the ego vehicle 123.

The communication unit 145 transmits and receives data to and from a network 105 or to another communication channel. In some embodiments, the communication unit 145 may include a DSRC transmitter, a DSRC receiver and other hardware or software necessary to make the ego vehicle 123 a DSRC-equipped device. In some embodiments, the medic system 199 is operable to control all or some of the operation of the communication unit 145.

In some embodiments, the communication unit 145 includes a port for direct physical connection to the network 105 or to another communication channel. For example, the communication unit 145 includes a USB, SD, CAT-5, or similar port for wired communication with the network 105. In some embodiments, the communication unit 145 includes a wireless transceiver for exchanging data with the network 105 or other communication channels using one or more wireless communication methods, including: IEEE 802.11; IEEE 802.16, BLUETOOTH®; EN ISO 14906:2004 Electronic Fee Collection—Application interface EN 11253: 2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); the communication method described in U.S. patent application Ser. No. 14/471, 387 filed on Aug. 28, 2014 and entitled "Full-Duplex Coordination System"; or another suitable wireless communication method.

In some embodiments, the communication unit 145 includes a radio that is operable to transmit and receive V2X messages via the network 105. For example, the communication unit 145 includes a radio that is operable to transmit and receive any type of V2X communication described above for the network 105.

In some embodiments, the communication unit 145 includes a full-duplex coordination system as described in U.S. Pat. No. 9,369,262 filed on Aug. 28, 2014 and entitled "Full-Duplex Coordination System," the entirety of which is incorporated herein by reference. In some embodiments, some, or all of the communications necessary to execute the methods described herein are executed using full-duplex wireless communication as described in U.S. Pat. No. 9,369, 262.

In some embodiments, the communication unit 145 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some embodiments, the communication unit 145 includes a wired port and a wireless transceiver. The communication unit 145 also provides other conventional connections to the network 105 for distribution of files or media objects using standard network protocols including TCP/IP, HTTP, HTTPS, and SMTP, millimeter wave, DSRC, etc.

In some embodiments, the communication unit 145 includes a V2X radio. The V2X radio is a hardware unit that includes one or more transmitters and one or more receivers that is operable to send and receive any type of V2X message. In some embodiments, the V2X radio is a C-V2X radio that is operable to send and receive C-V2X messages. In some embodiments, the C-V2X radio is operable to send and receive C-V2X messages on the upper 30 MHz of the 5.9 GHz band (i.e., 5.895-5.925 GHz). In some embodiments, some or all of the wireless messages described above with reference to the method 300 depicted in FIG. 3 are transmitted by the C-V2X radio on the upper 30 MHz of the 5.9 GHz band (i.e., 5.895-5.925 GHz) as directed by the medic system 199.

In some embodiments, the V2X radio includes a DSRC transmitter and a DSRC receiver. The DSRC transmitter is operable to transmit and broadcast DSRC messages over the 5.9 GHz band. The DSRC receiver is operable to receive DSRC messages over the 5.9 GHz band. In some embodiments, the DSRC transmitter and the DSRC receiver operate on some other band which is reserved exclusively for DSRC.

In some embodiments, the V2X radio includes a non-transitory memory which stores digital data that controls the frequency for broadcasting BSMs or CPMs. In some embodiments, the non-transitory memory stores a buffered version of the GPS data for the ego vehicle 123 so that the GPS data for the ego vehicle 123 is broadcast as an element of the BSMs or CPMs which are regularly broadcast by the V2X radio (e.g., at an interval of once every 0.10 seconds).

In some embodiments, the V2X radio includes any hardware or software which is necessary to make the ego vehicle 123 compliant with the DSRC standards or any other wireless communication standard that applies to wireless vehicular communications. In some embodiments, the standard-compliant GPS unit 150 is an element of the V2X radio.

The memory 127 may include a non-transitory storage medium. The memory 127 may store instructions or data that may be executed by the processor 125. The instructions or data may include code for performing the techniques described herein. The memory 127 may be a dynamic random-access memory (DRAM) device, a static random-access memory (SRAM) device, flash memory, or some other memory device. In some embodiments, the memory 127 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In some embodiments, the memory 127 may store any or all of the digital data or information described herein.

As depicted in FIG. 1, the memory 127 stores the following digital data: the threshold data 196; the member data 171; the digital twin data 162; the V2X data 133; the GPS data (as an element of the ego sensor data 195); the analysis data 181; the GUI data 187; the NLP data 183; the reaction data 173; the medical conditions data 174; the profile data 184; the remote help data 175; the routing data 176; the remote sensor data 193; the roadway data 154; the ego sensor data 195; and the cabin data 155. The system data 129 includes some or all of this digital data. In some embodiments, the V2X messages (or C-V2X messages or the set of wireless messages) described herein are also stored in the memory 127. The above-described elements of the memory 127 were described above, and so, those descriptions will not be repeated here.

Some or all of this digital data can be organized in a data structure that is stored in the memory 127 in some embodiments.

In some embodiments, the ego vehicle 123 includes a vehicle control system 153. A vehicle control system 153 includes one or more ADAS systems or an autonomous driving system.

Examples of an ADAS system include one or more of the following elements of a vehicle: an adaptive cruise control ("ACC") system; an adaptive high beam system; an adaptive light control system; an automatic parking system; an automotive night vision system; a blind spot monitor; a collision avoidance system; a crosswind stabilization system; a driver drowsiness medic system; a driver monitoring system; an emergency driver assistance system; a forward collision warning system; an intersection assistance system; an intelligent speed adaption system; a lane keep assistance ("LKA") system; a pedestrian protection system; a traffic sign recognition system; a turning assistant; and a wrong-way driving warning system. Other types of ADAS systems are possible. This list is illustrative and not exclusive.

An ADAS system is an onboard system that is operable to identify one or more factors (e.g., using one or more onboard vehicle sensors) affecting the ego vehicle 123 and modify (or control) the operation of its host vehicle (e.g., the ego vehicle 123) to respond to these identified factors. Described generally, ADAS system functionality includes the process of (1) identifying one or more factors affecting the ego vehicle and (2) modifying the operation of the ego vehicle, or some component of the ego vehicle, based on these identified factors.

For example, an ACC system installed and operational in an ego vehicle may identify that a subject vehicle being followed by the ego vehicle with the cruise control system engaged has increased or decreased its speed. The ACC system may modify the speed of the ego vehicle based on the change in speed of the subject vehicle, and the detection of this change in speed and the modification of the speed of the ego vehicle is an example the ADAS system functionality of the ADAS system.

Similarly, an ego vehicle 123 may have a LKA system installed and operational in an ego vehicle 123 may detect, using one or more external cameras of the ego vehicle 123, an event in which the ego vehicle 123 is near passing a center yellow line which indicates a division of one lane of travel from another lane of travel on a roadway. The LKA system may provide a notification to a driver of the ego vehicle 123 that this event has occurred (e.g., an audible noise or graphical display) or take action to prevent the ego vehicle 123 from actually passing the center yellow line such as making the steering wheel difficult to turn in a direction that would move the ego vehicle over the center yellow line or actually moving the steering wheel so that the ego vehicle 123 is further away from the center yellow line but still safely positioned in its lane of travel. The process of identifying the event and acting responsive to this event is an example of the ADAS system functionality provided by the LKA system.

The other ADAS systems described above each provide their own examples of ADAS system functionalities which are known in the art, and so, these examples of ADAS system functionality will not be repeated here.

In some embodiments, the ADAS system includes any software or hardware included in the vehicle that makes that vehicle be an autonomous vehicle or a semi-autonomous vehicle. In some embodiments, an autonomous driving system is a collection of ADAS systems which provides sufficient ADAS functionality to the ego vehicle 123 to render the ego vehicle 123 an autonomous or semi-autonomous vehicle.

An autonomous driving system includes a set of ADAS systems whose operation render sufficient autonomous functionality to render the ego vehicle 123 an autonomous vehicle (e.g., a Level III autonomous vehicle or higher as defined by the National Highway Traffic Safety Administration and the Society of Automotive Engineers).

In some embodiments, the medic system 199 includes code and routines that are operable, when executed by the processor 125, to execute one or more steps of the example general method described herein. In some embodiments, the medic system 199 includes code and routines that are operable, when executed by the processor 125, to execute one or more steps of the method 300 described below with reference to FIG. 3. In some embodiments, the medic system 199 includes code and routines that are operable, when executed by the processor 125, to execute one or more steps of the method 400 described below with reference to FIGS. 4A, 4B, 4C, 4D, 4E, and 4F.

Figure 2:
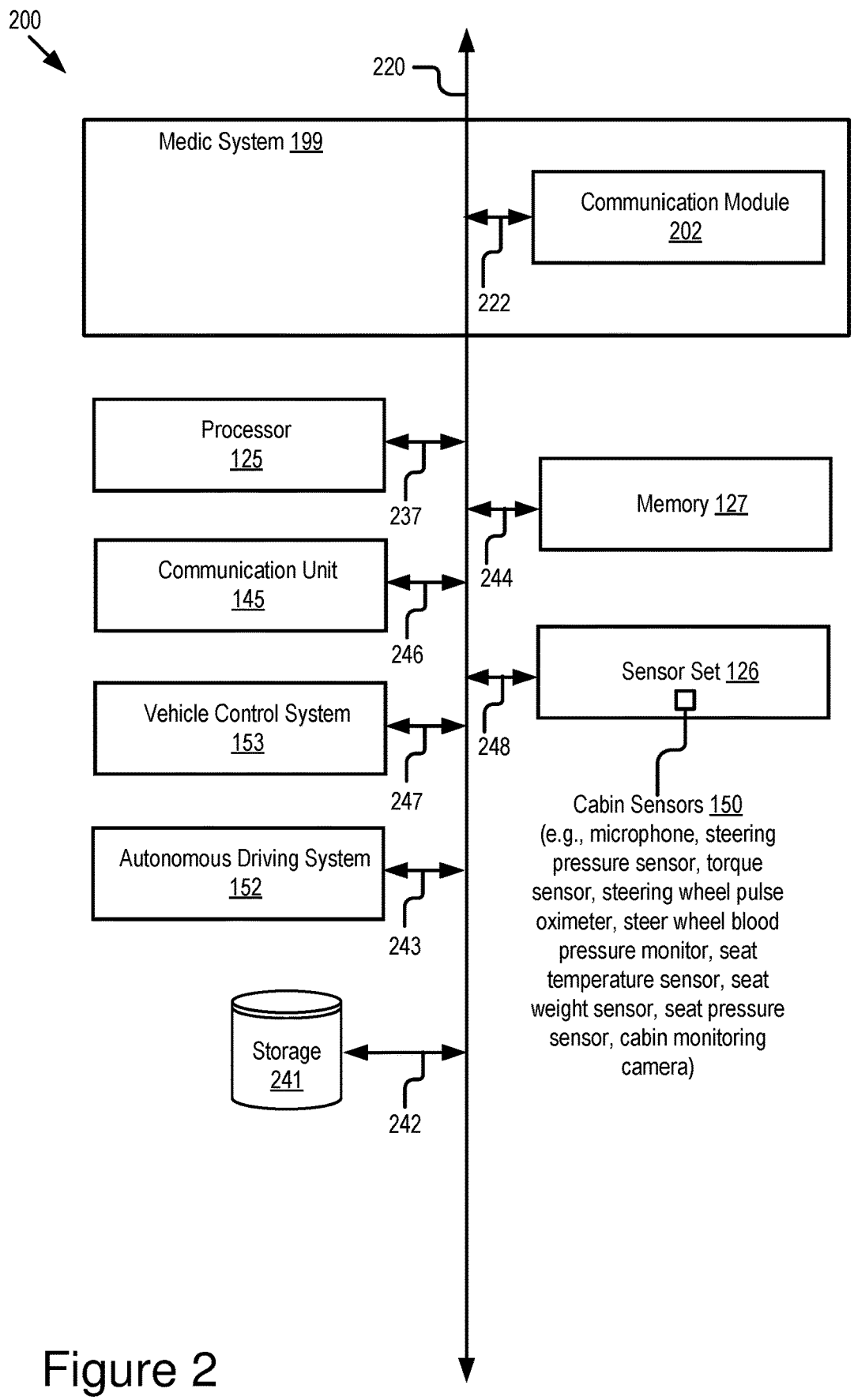
FIG. 2 is a block diagram illustrating an example computer system including a medic system according to some embodiments.

An example embodiment of the medic system 199 is depicted in FIG. 2. This embodiment is described in more detail below.

In some embodiments, the medic system 199 is an element of the onboard unit 139 or some other onboard vehicle computer. In some embodiments, the medic system 199 includes code and routines that are stored in the memory 127 and executed by the processor 125 or the onboard unit 139. In some embodiments, the medic system 199 is an element of an onboard unit of the ego vehicle 123 which executes the medic system 199 and controls the operation of the communication unit 145 of the ego vehicle 123 based at least in part on the output from executing the medic system 199.

In some embodiments, the medic system 199 is implemented using hardware including a field-programmable gate array ("FPGA") or an application-specific integrated circuit ("ASIC"). In some other embodiments, the medic system 199 is implemented using a combination of hardware and software.

The remote vehicle 124 includes elements and functionality which are similar to those described above for the ego vehicle 123, and so, those descriptions will not be repeated here. In some embodiments, one or more of the ego vehicle 123 and the remote vehicle 124 are members of a vehicular micro cloud 194. In some embodiments, the ego vehicle 123 and the remote vehicle 124 are not members of a vehicular micro cloud 194.

The roadway environment 140 is now described according to some embodiments. In some embodiments, some, or all of the ego vehicle 123 and the remote vehicle 124 (or a plurality of remote vehicles) are located in a roadway environment 140. In some embodiments, the roadway environment 140 includes one or more vehicular micro clouds 194. The roadway environment 140 is a portion of the real-world that includes a roadway, the ego vehicle 123 and the remote vehicle 124. The roadway environment 140 may include other elements such as roadway signs, environmental conditions, traffic, etc. The roadway environment 140 includes some or all of the tangible and/or measurable qualities described above with reference to the ego sensor data 195 and the remote sensor data 193. The remote sensor data 193 includes digital data that describes the sensor measurements recorded by the sensor set 126 of the remote vehicle 124.

In some embodiments, the real-world includes the real of human experience comprising physical objects and excludes artificial environments and "virtual" worlds such as computer simulations.

In some embodiments, the roadway environment 140 includes a roadway device (e.g., a roadside unit or some other processor-based computing system) that in includes an edge server 198. In some embodiments, the edge server 198 is a connected processor-based computing device that includes an instance of the medic system 199 and the other elements described above with reference to the ego vehicle 123 (e.g., a processor 125, a memory 127 storing the system data 129, a communication unit 145, etc.). In some embodiments, the roadway device is a member of the vehicular micro cloud 194.

In some embodiments, the edge server 198 includes one or more of the following elements: a hardware server; a personal computer; a laptop; a device such as a roadside unit; or any other processor-based connected device that is not a member of the vehicular micro cloud 194 and includes an instance of the medic system 199 and a non-transitory memory that stores some or all of the digital data that is stored by the memory 127 of the ego vehicle 123 or otherwise described herein. For example, the memory 127 stores the system data 129. The system data 129 includes some or all of the digital data depicted in FIG. 1 as being stored by the memory 127.

In some embodiments, the edge server 198 includes a backbone network. In some embodiments, the edge server 198 includes one or more of the following: an instance of the medic system 199; an MSPF system 138; a remote system 149; and a non-transitory memory storing system data 129. The functionality of these elements was described above with reference to the ego vehicle 123 and the example general method, and so, those descriptions will not be repeated here.

In some embodiments, the edge server 198 is operable to provide any other functionality described herein. For example, the edge server 198 is operable to execute some or all of the steps of the methods described herein.

In some embodiments, the cloud server 103 one or more of the following: a hardware server; a personal computer; a laptop; a device such as a roadside unit; or any other processor-based connected device that is not a member of the vehicular micro cloud 194 and includes an instance of the medic system 199 and a non-transitory memory that stores some or all of the digital data that is stored by the memory 127 of the ego vehicle 123 or otherwise described herein.

In some embodiments, the cloud server 103 includes one or more of the following elements: an instance of the medic system 199; an MSPF system 138; a remote system 149; and a non-transitory memory storing system data 129. The functionality of these elements was described above with reference to the ego vehicle 123 and the example general method, and so, those descriptions will not be repeated here.

In some embodiments, the cloud server 103 is operable to provide any other functionality described herein. For example, the cloud server 103 is operable to execute some or all of the steps of the methods described herein.

In some embodiments, the vehicular micro cloud 194 is stationary. In other words, in some embodiments the vehicular micro cloud 194 is a "stationary vehicular micro cloud." A stationary vehicular micro cloud is a wireless network system in which a plurality of connected vehicles (such as the ego vehicle 123, the remote vehicle 124, etc.), and optionally devices such as a roadway device, form a cluster of interconnected vehicles that are located at a same geographic region. These connected vehicles (and, optionally, connected devices) are interconnected via C-V2X, Wi-Fi, mmWave, DSRC or some other form of V2X wireless communication. For example, the connected vehicles are interconnected via a V2X network which may be the network 105 or some other wireless network that is only accessed by the members of the vehicular micro cloud 194 and not non-members such as the cloud server 103. Connected vehicles (and devices such as a roadside unit) which are members of the same stationary vehicular micro cloud make their unused computing resources available to the other members of the stationary vehicular micro cloud.

In some embodiments, the vehicular micro cloud 194 is "stationary" because the geographic location of the vehicular micro cloud 194 is static; different vehicles constantly enter and exit the vehicular micro cloud 194 over time. This means that the computing resources available within the vehicular micro cloud 194 is variable based on the traffic patterns for the geographic location at various times of day: increased traffic corresponds to increased computing resources because more vehicles will be eligible to join the vehicular micro cloud 194; and decreased traffic corresponds to decreased computing resources because less vehicles will be eligible to join the vehicular micro cloud 194.

In some embodiments, the V2X network is a non-infrastructure network. A non-infrastructure network is any conventional wireless network that does not include infrastructure such as cellular towers, servers, or server farms. For example, the V2X network specifically does not include a mobile data network including third generation (3G), fourth generation (4G), fifth generation (5G), long-term evolution (LTE), Voice-over-LTE (VoLTE) or any other mobile data network that relies on infrastructure such as cellular towers, hardware servers or server farms.

In some embodiments, the non-infrastructure network includes Bluetooth® communication networks for sending and receiving data including via one or more of DSRC, mmWave, full-duplex wireless communication and any other type of wireless communication that does not include infrastructure elements. The non-infrastructure network may include vehicle-to-vehicle communication such as a Wi-Fi™ network shared among two or more vehicles 123, 124.

In some embodiments, the wireless messages described herein are encrypted themselves or transmitted via an encrypted communication provided by the network 105. In some embodiments, the network 105 may include an encrypted virtual private network tunnel ("VPN tunnel") that does not include any infrastructure components such as network towers, hardware servers or server farms. In some embodiments, the medic system 199 includes encryption keys for encrypting wireless messages and decrypting the wireless messages described herein.

Referring now to FIG. 2, depicted is a block diagram illustrating an example computer system 200 including a medic system 199 according to some embodiments.

In some embodiments, the computer system 200 may include a special-purpose computer system that is programmed to perform one or more of the following: one or more steps of one or more of the method 300 described herein with reference to FIG. 3; one or more steps of one or more of the method 400 described herein with reference to FIGS. 4A, 4B, 4C, 4D, 4E, and 4F; and the example general method described herein.

In some embodiments, the computer system 200 may include a processor-based computing device. For example, the computer system 200 may include an onboard vehicle computer system of the ego vehicle 123 or the remote vehicle 124.

The computer system 200 may include one or more of the following elements according to some examples: the medic system 199; a processor 125; a communication unit 145; a vehicle control system 153; a storage 241; and a memory 127. The components of the computer system 200 are communicatively coupled by a bus 220.

In some embodiments, the computer system 200 includes additional elements such as those depicted in FIG. 1 as elements of the medic system 199.

In the illustrated embodiment, the processor 125 is communicatively coupled to the bus 220 via a signal line 237. The communication unit 145 is communicatively coupled to the bus 220 via a signal line 246. The vehicle control system 153 is communicatively coupled to the bus 220 via a signal line 247. The storage 241 is communicatively coupled to the bus 220 via a signal line 242. The memory 127 is communicatively coupled to the bus 220 via a signal line 244. The sensor set 126 is communicatively coupled to the bus 220 via a signal line 248. The autonomous driving system 152 is communicatively coupled to the bus 220 via a signal line 243.

In some embodiments, the sensor set 126 includes standard-compliant GPS unit. In some embodiments, the communication unit 145 includes a network sniffer.

The following elements of the computer system 200 were described above with reference to FIG. 1, and so, these descriptions will not be repeated here: the processor 125; the communication unit 145; the vehicle control system 153; the memory 127; the sensor set 126; and the autonomous driving system 152.

The storage 241 can be a non-transitory storage medium that stores data for providing the functionality described herein. The storage 241 may be a DRAM device, a SRAM device, flash memory, or some other memory devices. In some embodiments, the storage 241 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In some embodiments, the medic system 199 includes code and routines that are operable, when executed by the processor 125, to cause the processor 125 to execute one or more steps of the method 300 described herein with reference to FIG. 3. In some embodiments, the medic system 199 includes code and routines that are operable, when executed by the processor 125, to cause the processor 125 to execute one or more steps of the method 400 described herein with reference to FIGS. 4A, 4B, 4C, 4D, 4E, and 4F. In some embodiments, the medic system 199 includes code and routines that are operable, when executed by the processor 125, to cause the processor 125 to execute one or more steps of the example general method.

In the illustrated embodiment shown in FIG. 2, the medic system 199 includes a communication module 202.

The communication module 202 can be software including routines for handling communications between the medic system 199 and other components of the computer system 200. In some embodiments, the communication module 202 can be a set of instructions executable by the processor 125 to provide the functionality described below for handling communications between the medic system 199 and other components of the computer system 200. In some embodiments, the communication module 202 can be stored in the memory 127 of the computer system 200 and can be accessible and executable by the processor 125. The communication module 202 may be adapted for cooperation and communication with the processor 125 and other components of the computer system 200 via signal line 222.

The communication module 202 sends and receives data, via the communication unit 145, to and from one or more elements of the operating environment 100.

In some embodiments, the communication module 202 receives data from components of the medic system 199 and stores the data in one or more of the storage 241 and the memory 127.

In some embodiments, the communication module 202 may handle communications between components of the medic system 199 or the computer system 200.

Referring now to FIG. 3, depicted is a flowchart of an example method 300 according to some embodiments. The method 300 includes step 305, step 310, and step 315 as depicted in FIG. 3. The steps of the method 300 may be executed in any order, and not necessarily those depicted in FIG. 3. In some embodiments, one or more of the steps are skipped or modified in ways that are described herein or known or otherwise determinable by those having ordinary skill in the art.

Referring now to FIGS. 4A, 4B, 4C, 4D, 4E, and 4F depicted is a flowchart of an example method 400 according to some embodiments. The method 400 includes step 405, step 410, step 415, step 420, step 425, step 430, step 435, step 440, step 445, step 450, step 455, step 460, step 470, step 472, step 475, step 480, step 485, step 487, step 489, step 491, step 492, step 495, and step 497 as depicted in FIGS. 4A, 4B, 4C, 4D, 4E, and 4F. The steps of the method 400 may be executed in any order, and not necessarily those depicted in FIGS. 4A, 4B, 4C, 4D, 4E, and 4F. In some embodiments, one or more of the steps are skipped or modified in ways that are described herein or known or otherwise determinable by those having ordinary skill in the art.

Example differences in technical effect between the methods 300, 400, the example general method and the prior art are described below. These examples are illustrative and not exhaustive of the possible differences.

The existing solutions do not utilize vehicular micro clouds to implement functionality such as that provided by the medic system. The existing solutions also do not use digital twin simulations or other methods described herein to determine one or more of the following: analysis data; reaction data; and routing data.

The existing references also do not describe vehicular micro clouds as described herein. Some of the existing solutions require the use of vehicle platooning. A platoon is not a vehicular micro cloud and does not provide the benefits of a vehicular micro cloud, and some embodiments of the medic system that require a vehicular micro cloud. For example, among various differences between a platoon and a vehicular micro cloud, a platoon does not include a hub or a vehicle that provides the functionality of a hub vehicle. By comparison, in some embodiments the medic system includes codes and routines that are operable, when executed by a processor, to cause the processor to utilize vehicular micro clouds to resolve version differences among common vehicle applications installed in different connected vehicles.

The existing solutions do not describe, among other things, overriding a protocol to decrease an autonomy level of the ego vehicle responsive to inattentiveness of the driver to a driving interface of the ego vehicle so that the driver can be inattentive to the driving interface and the autonomy level is not decreased.

These examples are intended to be illustrative and not limiting.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the present embodiments can be described above primarily with reference to user interfaces and particular hardware. However, the present embodiments can apply to any type of computer system that can receive data and commands, and any peripheral devices providing services.

Reference in the specification to "some embodiments" or "some instances" means that a particular feature, structure, or characteristic described in connection with the embodiments or instances can be included in at least one embodiment of the description. The appearances of the phrase "in some embodiments" in various places in the specification are not necessarily all referring to the same embodiments.

Some portions of the detailed descriptions that follow are presented in terms of algorithms and symbolic representations of operations on data bits within a computer memory. These algorithmic descriptions and representations are the means used by those skilled in the data processing arts to convey the substance of their work most effectively to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present embodiments of the specification can also relate to an apparatus for performing the operations herein. This apparatus may be specially constructed for the required purposes, or it may include a general-purpose computer selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus.

The specification can take the form of some entirely hardware embodiments, some entirely software embodiments or some embodiments containing both hardware and software elements. In some preferred embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A medic system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited, to keyboards, displays, pointing devices, etc.) can be coupled to the system either directly or through intervening I/O controllers.

Network adapters may also be coupled to the system to enable the medic system to become coupled to other medic systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the embodiments of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to embodiment in any specific programming language, or for any specific operating system or environment. Accordingly, the disclosure is intended to be illustrative, but not limiting, of the scope of the specification, which is set forth in the following claims.

What is claimed is:

1. A method executed by a processor, the method comprising:
    determining, by the processor, that a driver of an ego vehicle is experiencing a debilitating medical condition;
    overriding a protocol to decrease an autonomy level of the ego vehicle responsive to inattentiveness of the driver to a driving interface of the ego vehicle so that the driver can be inattentive to the driving interface and the autonomy level is not decreased; and
    modifying an operation of an autonomous driving system of the ego vehicle to increase the autonomy level of the ego vehicle to decrease a driving responsibility of the driver responsive to the debilitating medical condition.

2. The method of claim 1, wherein inattentiveness includes a level of attention to the driving interface that fails to satisfy a threshold.

3. The method of claim 1, wherein overriding the protocol enables the driver to be inattentive to the driving interface and the autonomy level of the ego vehicle is not decreased.

4. The method of claim 1, wherein increasing the autonomy level of the ego vehicle includes maximizing the autonomy level of the ego vehicle.

5. The method of claim 1, further comprising identifying a remote driver of the ego vehicle, disabling the driving interface of the ego vehicle, and enabling the remote driver to control a driving operation of the ego vehicle from a remote location.

6. The method of claim 1, further comprising disabling the driving interface of the ego vehicle and causing the autonomous driving system of the ego vehicle to drive the ego vehicle to a safe location.

7. The method of claim 1, further comprising causing the autonomous driving system of the ego vehicle to drive the ego vehicle to an original destination.

8. The method of claim 1, further comprising initiating a telehealth appointment with a medical service provider.

9. The method of claim 1, further comprising identifying a remote medical service provider and causing the ego vehicle to be driven to an intercept location to meet the remote medical service provider.

10. The method of claim 9, further comprising identifying a remote driver of the ego vehicle, disabling the driving interface of the ego vehicle, and enabling the remote driver to control the operation of the ego vehicle from a remote location and drive the ego vehicle to the intercept location.

11. The method of claim 9, further comprising disabling the driving interface of the ego vehicle and causing the autonomous driving system of the ego vehicle to drive the ego vehicle to the intercept location.

12. The method of claim 9, wherein the remote medical service provider is an ambulatory service provider.

13. The method of claim 9, wherein the intercept location is a geographic location on a roadway that is along an intercept course driven by the ego vehicle and the remote medical service provider.

14. The method of claim 1, wherein at least one step of the method is executed by a vehicular micro cloud.

15. The method of claim 1, wherein at least one step of the method is executed by a processor-based computing device selected from a group including: an edge server; a cloud server; and a roadside unit.

16. The method of claim 1, wherein a first degree of increase in the autonomy of the ego vehicle responsive to the debilitating medical condition is inversely proportional to a second degree of decrease in a driving ability of the driver based on the debilitating medical condition.

17. The method of claim 1, further comprising determining how soon the debilitating medical condition will affect the driver.

18. The method of claim 1, further comprising receiving feedback from the driver about one or more of whether they believe they are experiencing the debilitating medical condition and an immanency of the debilitating medical condition to affect their driving ability.

19. A system comprising:

a non-transitory memory;

and a processor communicatively coupled to the non-transitory memory, wherein the non-transitory memory stores computer readable code that is operable, when executed by the processor, to cause the processor to execute steps including:

determining that a driver of an ego vehicle is experiencing a debilitating medical condition;

overriding a protocol to decrease an autonomy level of the ego vehicle responsive to inattentiveness of the driver to a driving interface of the ego vehicle so that the driver can be inattentive to the driving interface and the autonomy level is not decreased; and modifying an operation of an autonomous driving system of the ego vehicle to increase the autonomy level of the ego vehicle to decrease a driving responsibility of the driver responsive to the debilitating medical condition.

20. A computer program product including computer code stored on a non-transitory memory that is operable, when executed by a processor, to cause the processor to execute operations including:

determining that a driver of an ego vehicle is experiencing a debilitating medical condition;

overriding a protocol to decrease an autonomy level of the ego vehicle responsive to inattentiveness of the driver to a driving interface of the ego vehicle so that the driver can be inattentive to the driving interface and the autonomy level is not decreased; and modifying an operation of an autonomous driving system of the ego vehicle to increase the autonomy level of the ego vehicle to decrease a driving responsibility of the driver responsive to the debilitating medical condition.

* * * * *